United States Patent [19]
Murphy et al.

[11] Patent Number: 6,048,689
[45] Date of Patent: Apr. 11, 2000

[54] METHOD FOR IDENTIFYING VARIATIONS IN POLYNUCLEOTIDE SEQUENCES

[75] Inventors: Patricia D. Murphy, Slingerlands, N.Y.; Marga B. White, Frederick, Md.

[73] Assignee: Gene Logic, Inc., Gaithersburg, Md.

[21] Appl. No.: 08/825,487

[22] Filed: Mar. 28, 1997

[51] Int. Cl.$^7$ ..................................................... C12Q 1/68
[52] U.S. Cl. ........................... 435/6; 435/91.2; 536/24.3; 536/24.33; 935/77; 935/78
[58] Field of Search ................... 435/6, 91.2; 536/24.33, 536/24.3; 935/77, 78

[56] References Cited

U.S. PATENT DOCUMENTS

| | | | |
|---|---|---|---|
| 4,683,202 | 7/1987 | Mullis | 435/91 |
| 5,217,863 | 6/1993 | Cotton et al. | 435/6 |
| 5,498,324 | 3/1996 | Yeung et al. | 204/452 |
| 5,545,527 | 8/1996 | Stevens et al. | 435/6 |
| 5,561,058 | 10/1996 | Gelfand et al. | 435/912 |
| 5,582,989 | 12/1996 | Caskey et al. | 435/6 |
| 5,589,330 | 12/1996 | Shuber | 435/5 |
| 5,654,155 | 8/1997 | Murphy et al. | 435/6 |
| 5,710,001 | 1/1998 | Skolnick et al. | 435/6 |
| 5,750,400 | 5/1998 | Murphy et al. | 435/6 |

OTHER PUBLICATIONS

Struewing et al. Am. J. Hum. Genet. 57:1–5, Jul. 1995.
Hacia et al. Nature genetics 14:441–447, Dec. 1996.
Dowton et al. Clinical Chemistry 41:785–794, May 1995.
Sutcharitchan et al. Curr. Op. Hematol. 3:131–138, Mar. 1996.
Andersen, T. and Borresen, A., "Alterations of the TP53 Gene as a Potential Prognostic Marker in Breast Carcinomas," *Diagnostic Molecular Pathology* 4(3):203–211 (1995).
Easton et al., "Genetic Linkage Analysis in Familial Breast and Ovarian Cancer: Results from 214 Families," *American Journal of Human Genetics* 52:678–7091 (1993).
Friend et al., "Breast Cancer Information on the web," *Nature genetics* 11:238–239 (1995).
Gayther et al., "Rapid detection of Regionally Clustered Germ–Line BRCA 1 Mutations by Multiplex Heteroduplex analysis," *Am. J. Hum. Genet.* 58:451–456 (1996).
Hacia et al., "Detection of Heterozygous Mutations in BRCA 1 Using High Density Oligonucleotide Arrays and Two–Colour Fluorescence Analysis," *Nature Genetics* 14(4):441–447 (1996).
Merajver, S. and Petty, E., "Risk assessment and presymptomatic molecular diagnosis in hereditary breast cancer," *Clinics in Lab. Med.* 16(1):139–167 (1996).
Michalowsky et al., "Combinatorial Probes for Identifications of > 100 Known Mutations in Hundreds of patients Samples Simultaneousl Using MASDA (Multiplex Allele–Specific Diagnostic Assay)," *American Journal of Human Genetics* 59(4):A272, poster 1573 (1996).
Sambrook et al., *Molecular Cloning: A Laboratory Manual*, Second Ed., Cold Spring Harbor Laboratory Press (1989).
Sheffield et al., "Attachment of a 40–base–pair G+C–rich sequence (GC–clamp) to genomic DNA fragments by the polymerase chain reaction results in improved detection of Single–base changes," *Proc. Natl. Acad. Sci. USA* 86:232–236 (1989).
Weber, B., "Genetic Testing for Breast Cancer," *Scientific American SCIENCE & MEDICINE* Jan.–Feb.:12–21 (1996).

*Primary Examiner*—Kenneth R. Horlick
*Assistant Examiner*—Janell E. Taylor
*Attorney, Agent, or Firm*—Albert P. Halluin; Howrey Simon Arnold & White, LLP.

[57] ABSTRACT

A step-wise integrated process for identifying sequence variations in polynucleotide sequences is disclosed. The identification process is composed of three stages, including allele specific hybridization assays of known sequence variations (Stage I), sequence variation locating assays (Stage II), and direct sequencing (Stage III). The methods can be used for efficient and accurate detection of mutations in any test gene sample.

25 Claims, 10 Drawing Sheets

FIG. 1A

| | |
|---|---|
| AGCTCGCTGA GACTTCCTGG ACCCCGCACC AGGCTGTGGG GTTTCTCAGA TAACTGGGCC | 60 |
| CCTGCGCTCA GGAGGCCTTC ACCCTCTGCT CTGGGTAAAG TTCATTGGAA CAGAAAGAA | 119 |
| ATG GAT TTA TCT GCT CTT CGC GTT GAA GAA GTA CAA AAT GTC ATT AAT<br>Met Asp Leu Ser Ala Leu Arg Val Glu Glu Val Gln Asn Val Ile Asn<br>1               5                    10                 15 | 167 |
| GCT ATG CAG AAA ATC TTA GAG TGT CCC ATC TGT CTG GAG TTG ATC AAG<br>Ala Met Gln Lys Ile Leu Glu Cys Pro Ile Cys Leu Glu Leu Ile Lys<br>           20                   25                 30 | 215 |
| GAA CCT GTC TCC ACA AAG TGT GAC CAC ATA TTT TGC AAA TTT TGC ATG<br>Glu Pro Val Ser Thr Lys Cys Asp His Ile Phe Cys Lys Phe Cys Met<br>        35                   40                 45 | 263 |
| CTG AAA CTT CTC AAC CAG AAG AAA GGG CCT TCA CAG TGT CCT TTA TGT<br>Leu Lys Leu Leu Asn Gln Lys Lys Gly Pro Ser Gln Cys Pro Leu Cys<br>        50                   55                 60 | 311 |
| AAG AAT GAT ATA ACC AAA AGG AGC CTA CAA GAA AGT ACG AGA TTT AGT<br>Lys Asn Asp Ile Thr Lys Arg Ser Leu Gln Glu Ser Thr Arg Phe Ser<br>65                70                   75                80 | 359 |
| CAA CTT GTT GAA GAG CTA TTG AAA ATC ATT TGT GCT TTT CAG CTT GAC<br>Gln Leu Val Glu Glu Leu Leu Lys Ile Ile Cys Ala Phe Gln Leu Asp<br>                 85                   90                 95 | 407 |
| ACA GGT TTG GAG TAT GCA AAC AGC TAT AAT TTT GCA AAA AAG GAA AAT<br>Thr Gly Leu Glu Tyr Ala Asn Ser Tyr Asn Phe Ala Lys Lys Glu Asn<br>               100                105              110 | 455 |
| AAC TCT CCT GAA CAT CTA AAA GAT GAA GTT TCT ATC ATC CAA AGT ATG<br>Asn Ser Pro Glu His Leu Lys Asp Glu Val Ser Ile Ile Gln Ser Met<br>               115                120              125 | 503 |
| GGC TAC AGA AAC CGT GCC AAA AGA CTT CTA CAG AGT GAA CCC GAA AAT<br>Gly Tyr Arg Asn Arg Ala Lys Arg Leu Leu Gln Ser Glu Pro Glu Asn<br>               130                135              140 | 551 |
| CCT TCC TTG CAG GAA ACC AGT CTC AGT GTC CAA CTC TCT AAC CTT GGA<br>Pro Ser Leu Gln Glu Thr Ser Leu Ser Val Gln Leu Ser Asn Leu Gly<br>145                150                155              160 | 599 |
| ACT GTG AGA ACT CTG AGG ACA AAG CAG CGG ATA CAA CCT CAA AAG ACG<br>Thr Val Arg Thr Leu Arg Thr Lys Gln Arg Ile Gln Pro Gln Lys Thr<br>               165                170              175 | 647 |
| TCT GTC TAC ATT GAA TTG GGA TCT GAT TCT TCT GAA GAT ACC GTT AAT<br>Ser Val Tyr Ile Glu Leu Gly Ser Asp Ser Ser Glu Asp Thr Val Asn<br>               180                185              190 | 695 |

FIG. 1B

| | | | | | | | | | | | | | | | |
|---|---|---|---|---|---|---|---|---|---|---|---|---|---|---|---|
| AAG | GCA | ACT | TAT | TGC | AGT | GTG | GGA | GAT | CAA | GAA | TTG | TTA | CAA | ATC | ACC | 743 |
| Lys | Ala | Thr | Tyr | Cys | Ser | Val | Gly | Asp | Gln | Glu | Leu | Leu | Gln | Ile | Thr | |
| | | 195 | | | | 200 | | | | | 205 | | | | | |
| CCT | CAA | GGA | ACC | AGG | GAT | GAA | ATC | AGT | TTG | GAT | TCT | GCA | AAA | AAG | GCT | 791 |
| Pro | Gln | Gly | Thr | Arg | Asp | Glu | Ile | Ser | Leu | Asp | Ser | Ala | Lys | Lys | Ala | |
| | | 210 | | | | | 215 | | | | | 220 | | | | |
| GCT | TGT | GAA | TTT | TCT | GAG | ACG | GAT | GTA | ACA | AAT | ACT | GAA | CAT | CAT | CAA | 839 |
| Ala | Cys | Glu | Phe | Ser | Glu | Thr | Asp | Val | Thr | Asn | Thr | Glu | His | His | Gln | |
| 225 | | | | | 230 | | | | | 235 | | | | | 240 | |
| CCC | AGT | AAT | AAT | GAT | TTG | AAC | ACC | ACT | GAG | AAG | CGT | GCA | GCT | GAG | AGG | 887 |
| Pro | Ser | Asn | Asn | Asp | Leu | Asn | Thr | Thr | Glu | Lys | Arg | Ala | Ala | Glu | Arg | |
| | | | | 245 | | | | | 250 | | | | | 255 | | |
| CAT | CCA | GAA | AAG | TAT | CAG | GGT | AGT | TCT | GTT | TCA | AAC | TTG | CAT | GTG | GAG | 935 |
| His | Pro | Glu | Lys | Tyr | Gln | Gly | Ser | Ser | Val | Ser | Asn | Leu | His | Val | Glu | |
| | | | 260 | | | | | 265 | | | | | 270 | | | |
| CCA | TGT | GGC | ACA | AAT | ACT | CAT | GCC | AGC | TCA | TTA | CAG | CAT | GAG | AAC | AGC | 983 |
| Pro | Cys | Gly | Thr | Asn | Thr | His | Ala | Ser | Ser | Leu | Gln | His | Glu | Asn | Ser | |
| | | | 275 | | | | | 280 | | | | | 285 | | | |
| AGT | TTA | TTA | CTC | ACT | AAA | GAC | AGA | ATG | AAT | GTA | GAA | AAG | GCT | GAA | TTC | 1031 |
| Ser | Leu | Leu | Leu | Thr | Lys | Asp | Arg | Met | Asn | Val | Glu | Lys | Ala | Glu | Phe | |
| | | 290 | | | | | 295 | | | | | 300 | | | | |
| TGT | AAT | AAA | AGC | AAA | CAG | CCT | GGC | TTA | GCA | AGG | AGC | CAA | CAT | AAC | AGA | 1079 |
| Cys | Asn | Lys | Ser | Lys | Gln | Pro | Gly | Leu | Ala | Arg | Ser | Gln | His | Asn | Arg | |
| 305 | | | | | 310 | | | | | 315 | | | | | 320 | |
| TGG | GCT | GGA | AGT | AAG | GAA | ACA | TGT | AAT | GAT | AGG | CGG | ACT | CCC | AGC | ACA | 1127 |
| Trp | Ala | Gly | Ser | Lys | Glu | Thr | Cys | Asn | Asp | Arg | Arg | Thr | Pro | Ser | Thr | |
| | | | | 325 | | | | | 330 | | | | | 335 | | |
| GAA | AAA | AAG | GTA | GAT | CTG | AAT | GCT | GAT | CCC | CTG | TGT | GAG | AGA | AAA | GAA | 1175 |
| Glu | Lys | Lys | Val | Asp | Leu | Asn | Ala | Asp | Pro | Leu | Cys | Glu | Arg | Lys | Glu | |
| | | | | 340 | | | | | 345 | | | | | 350 | | |
| TGG | AAT | AAG | CAG | AAA | CTG | CCA | TGC | TCA | GAG | AAT | CCT | AGA | GAT | ACT | GAA | 1223 |
| Trp | Asn | Lys | Gln | Lys | Leu | Pro | Cys | Ser | Glu | Asn | Pro | Arg | Asp | Thr | Glu | |
| | | | | 355 | | | | | 360 | | | | | 365 | | |
| GAT | GTT | CCT | TGG | ATA | ACA | CTA | AAT | AGC | AGC | ATT | CAG | AAA | GTT | AAT | GAG | 1271 |
| Asp | Val | Pro | Trp | Ile | Thr | Leu | Asn | Ser | Ser | Ile | Gln | Lys | Val | Asn | Glu | |
| | | | 370 | | | | | 375 | | | | | 380 | | | |
| TGG | TTT | TCC | AGA | AGT | GAT | GAA | CTG | TTA | GGT | TCT | GAT | GAC | TCA | CAT | GAT | 1319 |
| Trp | Phe | Ser | Arg | Ser | Asp | Glu | Leu | Leu | Gly | Ser | Asp | Asp | Ser | His | Asp | |
| 385 | | | | | 390 | | | | | 395 | | | | | 400 | |

FIG. 1C

```
GGG GAG TCT GAA TCA AAT GCC AAA GTA GCT GAT GTA TTG GAC GTT CTA       1367
Gly Glu Ser Glu Ser Asn Ala Lys Val Ala Asp Val Leu Asp Val Leu
                    405                 410                 415

AAT GAG GTA GAT GAA TAT TCT GGT TCT TCA GAG AAA ATA GAC TTA CTG       1415
Asn Glu Val Asp Glu Tyr Ser Gly Ser Ser Glu Lys Ile Asp Leu Leu
                420                 425                 430

GCC AGT GAT CCT CAT GAG GCT TTA ATA TGT AAA AGT GAA AGA GTT CAC       1463
Ala Ser Asp Pro His Glu Ala Leu Ile Cys Lys Ser Glu Arg Val His
            435                 440                 445

TCC AAA TCA GTA GAG AGT AAT ATT GAA GAC AAA ATA TTT GGG AAA ACC       1511
Ser Lys Ser Val Glu Ser Asn Ile Glu Asp Lys Ile Phe Gly Lys Thr
        450                 455                 460

TAT CGG AAG AAG GCA AGC CTC CCC AAC TTA AGC CAT GTA ACT GAA AAT       1559
Tyr Arg Lys Lys Ala Ser Leu Pro Asn Leu Ser His Val Thr Glu Asn
465                 470                 475                 480

CTA ATT ATA GGA GCA TTT GTT ACT GAG CCA CAG ATA ATA CAA GAG CGT       1607
Leu Ile Ile Gly Ala Phe Val Thr Glu Pro Gln Ile Ile Gln Glu Arg
                485                 490                 495

CCC CTC ACA AAT AAA TTA AAG CGT AAA AGG AGA CCT ACA TCA GGC CTT       1655
Pro Leu Thr Asn Lys Leu Lys Arg Lys Arg Arg Pro Thr Ser Gly Leu
                500                 505                 510

CAT CCT GAG GAT TTT ATC AAG AAA GCA GAT TTG GCA GTT CAA AAG ACT       1703
His Pro Glu Asp Phe Ile Lys Lys Ala Asp Leu Ala Val Gln Lys Thr
            515                 520                 525

CCT GAA ATG ATA AAT CAG GGA ACT AAC CAA ACG GAG CAG AAT GGT CAA       1751
Pro Glu Met Ile Asn Gln Gly Thr Asn Gln Thr Glu Gln Asn Gly Gln
        530                 535                 540

GTG ATG AAT ATT ACT AAT AGT GGT CAT GAG AAT AAA ACA AAA GGT GAT       1799
Val Met Asn Ile Thr Asn Ser Gly His Glu Asn Lys Thr Lys Gly Asp
545                 550                 555                 560

TCT ATT CAG AAT GAG AAA AAT CCT AAC CCA ATA GAA TCA CTC GAA AAA       1847
Ser Ile Gln Asn Glu Lys Asn Pro Asn Pro Ile Glu Ser Leu Glu Lys
                565                 570                 575

GAA TCT GCT TTC AAA ACG AAA GCT GAA CCT ATA AGC AGC AGT ATA AGC       1895
Glu Ser Ala Phe Lys Thr Lys Ala Glu Pro Ile Ser Ser Ser Ile Ser
                580                 585                 590

AAT ATG GAA CTC GAA TTA AAT ATC CAC AAT TCA AAA GCA CCT AAA AAG       1943
Asn Met Glu Leu Glu Leu Asn Ile His Asn Ser Lys Ala Pro Lys Lys
            595                 600                 605
```

FIG. 1D

```
AAT AGG CTG AGG AGG AAG TCT TCT ACC AGG CAT ATT CAT GCG CTT GAA      1991
Asn Arg Leu Arg Arg Lys Ser Ser Thr Arg His Ile His Ala Leu Glu
    610             615             620

CTA GTA GTC AGT AGA AAT CTA AGC CCA CCT AAT TGT ACT GAA TTG CAA      2039
Leu Val Val Ser Arg Asn Leu Ser Pro Pro Asn Cys Thr Glu Leu Gln
625             630             635             640

ATT GAT AGT TGT TCT AGC AGT GAA GAG ATA AAG AAA AAA AAG TAC AAC      2087
Ile Asp Ser Cys Ser Ser Ser Glu Glu Ile Lys Lys Lys Lys Tyr Asn
                645             650             655

CAA ATG CCA GTC AGG CAC AGC AGA AAC CTA CAA CTC ATG GAA GGT AAA      2135
Gln Met Pro Val Arg His Ser Arg Asn Leu Gln Leu Met Glu Gly Lys
            660             665             670

GAA CCT GCA ACT GGA GCC AAG AAG AGT AAC AAG CCA AAT GAA CAG ACA      2183
Glu Pro Ala Thr Gly Ala Lys Lys Ser Asn Lys Pro Asn Glu Gln Thr
        675             680             685

AGT AAA AGA CAT GAC AGT GAT ACT TTC CCA GAG CTG AAG TTA ACA AAT      2231
Ser Lys Arg His Asp Ser Asp Thr Phe Pro Glu Leu Lys Leu Thr Asn
    690             695             700

GCA CCT GGT TCT TTT ACT AAG TGT TCA AAT ACC AGT GAA CTT AAA GAA      2279
Ala Pro Gly Ser Phe Thr Lys Cys Ser Asn Thr Ser Glu Leu Lys Glu
705             710             715             720

TTT GTC AAT CCT AGC CTT CCA AGA GAA GAA AAA GAA GAG AAA CTA GAA      2327
Phe Val Asn Pro Ser Leu Pro Arg Glu Glu Lys Glu Glu Lys Leu Glu
                725             730             735

ACA GTT AAA GTG TCT AAT AAT GCT GAA GAC CCC AAA GAT CTC ATG TTA      2375
Thr Val Lys Val Ser Asn Asn Ala Glu Asp Pro Lys Asp Leu Met Leu
            740             745             750

AGT GGA GAA AGG GTT TTG CAA ACT GAA AGA TCT GTA GAG AGT AGC AGT      2423
Ser Gly Glu Arg Val Leu Gln Thr Glu Arg Ser Val Glu Ser Ser Ser
        755             760             765

ATT TCA CTG GTA CCT GGT ACT GAT TAT GGC ACT CAG GAA AGT ATC TCG      2471
Ile Ser Leu Val Pro Gly Thr Asp Tyr Gly Thr Gln Glu Ser Ile Ser
    770             775             780

TTA CTG GAA GTT AGC ACT CTA GGG AAG GCA AAA ACA GAA CCA AAT AAA      2519
Leu Leu Glu Val Ser Thr Leu Gly Lys Ala Lys Thr Glu Pro Asn Lys
785             790             795             800

TGT GTG AGT CAG TGT GCA GCA TTT GAA AAC CCC AAG GGA CTA ATT CAT      2567
Cys Val Ser Gln Cys Ala Ala Phe Glu Asn Pro Lys Gly Leu Ile His
                805             810             815
```

FIG. 1E

| | |
|---|---|
| GGT TGT TCC AAA GAT AAT AGA AAT GAC ACA GAA GGC TTT AAG TAT CCA<br>Gly Cys Ser Lys Asp Asn Arg Asn Asp Thr Glu Gly Phe Lys Tyr Pro<br>          820                   825                  830 | 2615 |
| TTG GGA CAT GAA GTT AAC CAC AGT CGG GAA ACA AGC ATA GAA ATG GAA<br>Leu Gly His Glu Val Asn His Ser Arg Glu Thr Ser Ile Glu Met Glu<br>          835                   840                  845 | 2663 |
| GAA AGT GAA CTT GAT GCT CAG TAT TTG CAG AAT ACA TTC AAG GTT TCA<br>Glu Ser Glu Leu Asp Ala Gln Tyr Leu Gln Asn Thr Phe Lys Val Ser<br>          850                   855                  860 | 2711 |
| AAG CGC CAG TCA TTT GCT CTG TTT TCA AAT CCA GGA AAT GCA GAA GAG<br>Lys Arg Gln Ser Phe Ala Leu Phe Ser Asn Pro Gly Asn Ala Glu Glu<br>865               870                   875                  880 | 2759 |
| GAA TGT GCA ACA TTC TCT GCC CAC TCT GGG TCC TTA AAG AAA CAA AGT<br>Glu Cys Ala Thr Phe Ser Ala His Ser Gly Ser Leu Lys Lys Gln Ser<br>                         885                   890                  895 | 2807 |
| CCA AAA GTC ACT TTT GAA TGT GAA CAA AAG GAA GAA AAT CAA GGA AAG<br>Pro Lys Val Thr Phe Glu Cys Glu Gln Lys Glu Glu Asn Gln Gly Lys<br>          900                   905                  910 | 2855 |
| AAT GAG TCT AAT ATC AAG CCT GTA CAG ACA GTT AAT ATC ACT GCA GGC<br>Asn Glu Ser Asn Ile Lys Pro Val Gln Thr Val Asn Ile Thr Ala Gly<br>          915                   920                  925 | 2903 |
| TTT CCT GTG GTT GGT CAG AAA GAT AAG CCA GTT GAT AAT GCC AAA TGT<br>Phe Pro Val Val Gly Gln Lys Asp Lys Pro Val Asp Asn Ala Lys Cys<br>          930                   935                  940 | 2951 |
| AGT ATC AAA GGA GGC TCT AGG TTT TGT CTA TCA TCT CAG TTC AGA GGC<br>Ser Ile Lys Gly Gly Ser Arg Phe Cys Leu Ser Ser Gln Phe Arg Gly<br>945               950                   955                  960 | 2999 |
| AAC GAA ACT GGA CTC ATT ACT CCA AAT AAA CAT GGA CTT TTA CAA AAC<br>Asn Glu Thr Gly Leu Ile Thr Pro Asn Lys His Gly Leu Leu Gln Asn<br>                    965                   970                  975 | 3047 |
| CCA TAT CGT ATA CCA CCA CTT TTT CCC ATC AAG TCA TTT GTT AAA ACT<br>Pro Tyr Arg Ile Pro Pro Leu Phe Pro Ile Lys Ser Phe Val Lys Thr<br>               980                   985                  990 | 3095 |
| AAA TGT AAG AAA AAT CTG CTA GAG GAA AAC TTT GAG GAA CAT TCA ATG<br>Lys Cys Lys Lys Asn Leu Leu Glu Glu Asn Phe Glu Glu His Ser Met<br>          995                   1000               1005 | 3143 |
| TCA CCT GAA AGA GAA ATG GGA AAT GAG AAC ATT CCA AGT ACA GTG AGC<br>Ser Pro Glu Arg Glu Met Gly Asn Glu Asn Ile Pro Ser Thr Val Ser<br>1010                  1015                 1020 | 3191 |

FIG. 1F

```
ACA ATT AGC CGT AAT AAC ATT AGA GAA AAT GTT TTT AAA GGA GCC AGC      3239
Thr Ile Ser Arg Asn Asn Ile Arg Glu Asn Val Phe Lys Gly Ala Ser
1025                1030                1035                1040

TCA AGC AAT ATT AAT GAA GTA GGT TCC AGT ACT AAT GAA GTG GGC TCC      3287
Ser Ser Asn Ile Asn Glu Val Gly Ser Ser Thr Asn Glu Val Gly Ser
                1045                1050                1055

AGT ATT AAT GAA ATA GGT TCC AGT GAT GAA AAC ATT CAA GCA GAA CTA      3335
Ser Ile Asn Glu Ile Gly Ser Ser Asp Glu Asn Ile Gln Ala Glu Leu
            1060                1065                1070

GGT AGA AAC AGA GGG CCA AAA TTG AAT GCT ATG CTT AGA TTA GGG GTT      3383
Gly Arg Asn Arg Gly Pro Lys Leu Asn Ala Met Leu Arg Leu Gly Val
        1075                1080                1085

TTG CAA CCT GAG GTC TAT AAA CAA AGT CTT CCT GGA AGT AAT TGT AAG      3431
Leu Gln Pro Glu Val Tyr Lys Gln Ser Leu Pro Gly Ser Asn Cys Lys
    1090                1095                1100

CAT CCT GAA ATA AAA AAG CAA GAA TAT GAA GAA GTA GTT CAG ACT GTT      3479
His Pro Glu Ile Lys Lys Gln Glu Tyr Glu Glu Val Val Gln Thr Val
1105                1110                1115                1120

AAT ACA GAT TTC TCT CCA TAT CTG ATT TCA GAT AAC TTA GAA CAG CCT      3527
Asn Thr Asp Phe Ser Pro Tyr Leu Ile Ser Asp Asn Leu Glu Gln Pro
                1125                1130                1135

ATG GGA AGT AGT CAT GCA TCT CAG GTT TGT TCT GAG ACA CCT GAT GAC      3575
Met Gly Ser Ser His Ala Ser Gln Val Cys Ser Glu Thr Pro Asp Asp
            1140                1145                1150

CTG TTA GAT GAT GGT GAA ATA AAG GAA GAT ACT AGT TTT GCT GAA AAT      3623
Leu Leu Asp Asp Gly Glu Ile Lys Glu Asp Thr Ser Phe Ala Glu Asn
        1155                1160                1165

GAC ATT AAG GAA AGT TCT GCT GTT TTT AGC AAA AGC GTC CAG AGA GGA      3671
Asp Ile Lys Glu Ser Ser Ala Val Phe Ser Lys Ser Val Gln Arg Gly
    1170                1175                1180

GAG CTT AGC AGG AGT CCT AGC CCT TTC ACC CAT ACA CAT TTG GCT CAG      3719
Glu Leu Ser Arg Ser Pro Ser Pro Phe Thr His Thr His Leu Ala Gln
1185                1190                1195                1200

GGT TAC CGA AGA GGG GCC AAG AAA TTA GAG TCC TCA GAA GAG AAC TTA      3767
Gly Tyr Arg Arg Gly Ala Lys Lys Leu Glu Ser Ser Glu Glu Asn Leu
                1205                1210                1215

TCT AGT GAG GAT GAA GAG CTT CCC TGC TTC CAA CAC TTG TTA TTT GGT      3815
Ser Ser Glu Asp Glu Glu Leu Pro Cys Phe Gln His Leu Leu Phe Gly
            1220                1225                1230
```

FIG. 1G

| | |
|---|---|
| AAA GTA AAC AAT ATA CCT TCT CAG TCT ACT AGG CAT AGC ACC GTT GCT<br>Lys Val Asn Asn Ile Pro Ser Gln Ser Thr Arg His Ser Thr Val Ala<br>         1235                   1240                1245 | 3863 |
| AAC GAG TGT CTG TCT AAG AAC ACA GAG GAG AAT TTA TTA TCA TTG AAG<br>Thr Glu Cys Leu Ser Lys Asn Thr Glu Glu Asn Leu Leu Ser Leu Lys<br>         1250                   1255                1260 | 3911 |
| AAT AGC TTA AAT GAC TGC AGT AAC CAG GTA ATA TTG GCA AAG GCA TCT<br>Asn Ser Leu Asn Asp Cys Ser Asn Gln Val Ile Leu Ala Lys Ala Ser<br>1265                   1270                 1275                1280 | 3959 |
| CAG GAA CAT CAC CTT AGT GAG GAA ACA AAA TGT TCT GCT AGC TTG TTT<br>Gln Glu His His Leu Ser Glu Glu Thr Lys Cys Ser Ala Ser Leu Phe<br>                   1285                1290                1295 | 4007 |
| TCT TCA CAG TGC AGT GAA TTG GAA GAC TTG ACT GCA AAT ACA AAC ACC<br>Ser Ser Gln Cys Ser Glu Leu Glu Asp Leu Thr Ala Asn Thr Asn Thr<br>         1300                   1305                1310 | 4055 |
| CAG GAT CCT TTC TTG ATT GGT TCT TCC AAA CAA ATG AGG CAT CAG TCT<br>Gln Asp Pro Phe Leu Ile Gly Ser Ser Lys Gln Met Arg His Gln Ser<br>               1315                   1320                1325 | 4103 |
| GAA AGC CAG GGA GTT GGT CTG AGT GAC AAG GAA TTG GTT TCA GAT GAT<br>Glu Ser Gln Gly Val Gly Leu Ser Asp Lys Glu Leu Val Ser Asp Asp<br>         1330                   1335                1340 | 4151 |
| GAA GAA AGA GGA ACG GGC TTG GAA GAA AAT AAT CAA GAA GAG CAA AGC<br>Glu Glu Arg Gly Thr Gly Leu Glu Glu Asn Asn Gln Glu Glu Gln Ser<br>1345                   1350                 1355                1360 | 4199 |
| ATG GAT TCA AAC TTA GGT GAA GCA GCA TCT GGG TGT GAG AGT GAA ACA<br>Met Asp Ser Asn Leu Gly Glu Ala Ala Ser Gly Cys Glu Ser Glu Thr<br>                   1365                1370                1375 | 4247 |
| AGC GTC TCT GAA GAC TGC TCA GGG CTA TCC TCT CAG AGT GAC ATT TTA<br>Ser Val Ser Glu Asp Cys Ser Gly Leu Ser Ser Gln Ser Asp Ile Leu<br>               1380                   1385                1390 | 4295 |
| ACC ACT CAG CAG AGG GAT ACC ATG CAA CAT AAC CTG ATA AAG CTC CAG<br>Thr Thr Gln Gln Arg Asp Thr Met Gln His Asn leu Ile Lys Leu Gln<br>               1395                   1400                1405 | 4343 |
| CAG GAA ATG GCT GAA CTA GAA GCT GTG TTA GAA CAG CAT GGG AGC CAG<br>Gln Glu Met Ala Glu Leu Glu Ala Val Leu Glu Gln His Gly Ser Gln<br>         1410                   1415                1420 | 4391 |
| CCT TCT AAC AGC TAC CCT TCC ATC ATA AGT GAC TCC TCT GCC CTT GAG<br>Pro Ser Asn Ser Tyr Pro Ser Ile Ile Ser Asp Ser Ser Ala Leu Glu<br>1425                   1430                 1435                1440 | 4439 |

FIG. 1H

| | |
|---|---|
| GAC CTG CGA AAT CCA GAA CAA AGC ACA TCA GAA AAA GCA GTA TTA ACT<br>Asp Leu Arg Asn Pro Glu Gln Ser Thr Ser Glu Lys Ala Val Leu Thr<br>              1445                      1450                     1455 | 4487 |
| TCA CAG AAA AGT AGT GAA TAC CCT ATA AGC CAG AAT CCA GAA GGC CTT<br>Ser Gln Lys Ser Ser Glu Tyr Pro Ile Ser Gln Asn Pro Glu Gly Leu<br>              1460                      1465                     1470 | 4535 |
| TCT GCT GAC AAG TTT GAG GTG TCT GCA GAT AGT TCT ACC AGT AAA AAT<br>Ser Ala Asp Lys Phe Glu Val Ser Ala Asp Ser Ser Thr Ser Lys Asn<br>              1475                      1480                     1485 | 4583 |
| AAA GAA CCA GGA GTG GAA AGG TCA TCC CCT TCT AAA TGC CCA TCA TTA<br>Lys Glu Pro Gly Val Glu Arg Ser Ser Pro Ser Lys Cys Pro Ser Leu<br>              1490                      1495                     1500 | 4631 |
| GAT GAT AGG TGG TAC ATG CAC AGT TGC TCT GGG AGT CTT CAG AAT AGA<br>Asp Asp Arg Trp Tyr Met His Ser Cys Ser Gly Ser Leu Gln Asn Arg<br>1505              1510                      1515                     1520 | 4679 |
| AAC TAC CCA TCT CAA GAG GAG CTC ATT AAG GTT GTT GAT GTG GAG GAG<br>Asn Tyr Pro Ser Gln Glu Glu Leu Ile Lys Val Val Asp Val Glu Glu<br>              1525                      1530                     1535 | 4727 |
| CAA CAG CTG GAA GAG TCT GGG CCA CAC GAT TTG ACG GAA ACA TCT TAC<br>Gln Gln Leu Glu Glu Ser Gly Pro His Asp Leu Thr Glu Thr Ser Tyr<br>              1540                      1545                     1550 | 4775 |
| TTG CCA AGG CAA GAT CTA GAG GGA ACC CCT TAC CTG GAA TCT GGA ATC<br>Leu Pro Arg Gln Asp Leu Glu Gly Thr Pro Tyr Leu Glu Ser Gly Ile<br>              1555                      1560                     1565 | 4823 |
| AGC CTC TTC TCT GAT GAC CCT GAA TCT GAT CCT TCT GAA GAC AGA GCC<br>Ser Leu Phe Ser Asp Asp Pro Glu Ser Asp Pro Ser Glu Asp Arg Ala<br>              1570                      1575                     1580 | 4871 |
| CCA GAG TCA GCT CGT GTT GGC AAC ATA CCA TCT TCA ACC TCT GCA TTG<br>Pro Glu Ser Ala Arg Val Gly Asn Ile Pro Ser Ser Thr Ser Ala Leu<br>1585              1590                      1595                     1600 | 4919 |
| AAA GTT CCC CAA TTG AAA GTT GCA GAA TCT GCC CAG GGT CCA GCT GCT<br>Lys Val Pro Gln Leu Lys Val Ala Glu Ser Ala Gln Gly Pro Ala Ala<br>              1605                      1610                     1615 | 4967 |
| GCT CAT ACT ACT GAT ACT GCT GGG TAT AAT GCA ATG GAA GAA AGT GTG<br>Ala His Thr Thr Asp Thr Ala Gly Tyr Asn Ala Met Glu Glu Ser Val<br>              1620                      1625                     1630 | 5015 |
| AGC AGG GAG AAG CCA GAA TTG ACA GCT TCA ACA GAA AGG GTC AAC AAA<br>Ser Arg Glu Lys Pro Glu Leu Thr Ala Ser Thr Glu Arg Val Asn Lys<br>              1635                      1640                     1645 | 5063 |

FIG. 11

```
AGA ATG TCC ATG GTG GTG TCT GGC CTG ACC CCA GAA GAA TTT ATG CTC    5111
Arg Met Ser Met Val Val Ser Gly Leu Thr Pro Glu Glu Phe Met Leu
    1650            1655                1660

GTG TAC AAG TTT GCC AGA AAA CAC CAC ATC ACT TTA ACT AAT CTA ATT    5159
Val Tyr Lys Phe Ala Arg Lys His His Ile Thr Leu Thr Asn Leu Ile
1665            1670                1675                1680

ACT GAA GAG ACT ACT CAT GTT GTT ATG AAA ACA GAT GCT GAG TTT GTG    5207
Thr Glu Glu Thr Thr His Val Val Met Lys Thr Asp Ala Glu Phe Val
                1685                1690                1695

TGT GAA CGG ACA CTG AAA TAT TTT CTA GGA ATT GCG GGA GGA AAA TGG    5255
Cys Glu Arg Thr Leu Lys Tyr Phe Leu Gly Ile Ala Gly Gly Lys Trp
            1700                1705                1710

GTA GTT AGC TAT TTC TGG GTG ACC CAG TCT ATT AAA GAA AGA AAA ATG    5303
Val Val Ser Tyr Phe Trp Val Thr Gln Ser Ile Lys Glu Arg Lys Met
            1715                1720                1725

CTG AAT GAG CAT GAT TTT GAA GTC AGA GGA GAT GTG GTC AAT GGA AGA    5351
Leu Asn Glu His Asp Phe Glu Val Arg Gly Asp Val Val Asn Gly Arg
            1730                1735                1740

AAC CAC CAA GGT CCA AAG CGA GCA AGA GAA TCC CAG GAC AGA AAG ATC    5399
Asn His Gln Gly Pro Lys Arg Ala Arg Glu Ser Gln Asp Arg Lys Ile
1745                1750                1755                1760

TTC AGG GGG CTA GAA ATC TGT TGC TAT GGG CCC TTC ACC AAC ATG CCC    5447
Phe Arg Gly Leu Glu Ile Cys Cys Tyr Gly Pro Phe Thr Asn Met Pro
                1765                1770                1775

ACA GAT CAA CTG GAA TGG ATG GTA CAG CTG TGT GGT GCT TCT GTG GTG    5495
Thr Asp Gln Leu Glu Trp Met Val Gln Leu Cys Gly Ala Ser Val Val
                1780                1785                1790

AAG GAG CTT TCA TCA TTC ACC CTT GGC ACA GGT GTC CAC CCA ATT GTG    5543
Lys Glu Leu Ser Ser Phe Thr Leu Gly Thr Gly Val His Pro Ile Val
            1795                1800                1805

GTT GTG CAG CCA GAT GCC TGG ACA GAG GAC AAT GGC TTC CAT GCA ATT    5591
Val Val Gln Pro Asp Ala Trp Thr Glu Asp Asn Gly Phe His Ala Ile
    1810                1815                1820

GGG CAG ATG TGT GAG GCA CCT GTG GTG ACC CGA GAG TGG GTG TTG GAC    5639
Gly Gln Met Cys Glu Ala Pro Val Val Thr Arg Glu Trp Val Leu Asp
    1825                1830                1835                1840
```

FIG. 1J

```
AGT GTA GCA CTC TAC CAG TGC CAG GAG CTG GAC ACC TAC CTG ATA CCC      5687
Ser Val Ala Leu Tyr Gln Cys Gln Glu Leu Asp Thr Tyr Leu Ile Pro
            1845            1850            1855

CAG ATC CCC CAC AGC CAC TAC TGA                                       5711
Gln Ile Pro His Ser His Tyr  *
            1860
```

METHOD FOR IDENTIFYING VARIATIONS IN POLYNUCLEOTIDE SEQUENCES

1. INTRODUCTION

The present invention relates to methods of detecting and identifying sequence variations in polynucleotide sequences. More specifically, this invention relates to a screening process whereby the presence of sequence variations is detected in sequential steps. The methods are applicable to detecting mutations in any isolated gene. The invention is described in detail, for the purpose of illustration and not by way of limitation, for detecting mutations in the human BRCA1 gene.

2. BACKGROUND OF THE INVENTION

An increasing number of genes which play a role in many different diseases are being identified. Detection of mutations in such genes is instrumental in determining susceptibility to or diagnosing these diseases. Some diseases, such as sickle cell disease, are monomorphic, i.e., the disease is generally caused by a single mutation present in the population. In such cases where one or only a few known mutations are responsible for the disease, methods for detecting the mutations are targeted to the site within the gene at which they are known to occur.

In many other cases, however, individuals affected by a given disease display extensive allelic heterogeneity. For example, more than 125 mutations in the human BRCA1 gene have been reported (Breast Cancer Information Core world wide web site at http://www.nchgr.nih.gov/dir/lab_transfer/bic, which became publicly available on Nov. 1, 1995; Friend, S. et al., 1995, Nature Genetics 11: 238). Mutations in the BRCA1 gene are thought to account for roughly 45% of inherited breast cancer and 80–90% of families with increased risk of early onset breast and ovarian cancer (Easton, 1993, et al., American Journal of Human Genetics 52: 678–701).

Other examples of genes for which the population displays extensive allelic heterogeneity and which have been implicated in disease include CFTR (cystic fibrosis), dystrophin (Duchenne muscular dystrophy, and Becker muscular dystrophy), and p53 (Li-Fraumeni syndrome).

Breast cancer is also an example of a disease in which, in addition to allelic heterogeneity, there is genetic heterogeneity. In addition to BRCA1, the BRCA2 and BRCA3 genes have been linked to breast cancer. Similarly, the NFI and NFII genes are involved in neurofibromatosis (types I and II, respectively).

Accuracy in detection of mutations is extremely important, particularly in clinical settings. Direct end-to-end sequencing of the gene potentially provides the most accurate results, given that an accurate reference sequence is available. However, sequencing can also be a cumbersome technique. Detection of one of many known or unknown mutations is further complicated when the gene is large and/or has a complex structure. The human BRCA1 gene, for example, is approximately 100,000 base pairs long and contains 24 exons (Weber, B., Science and Medicine, *Scientific American* January–February 1996, 12–21). Furthermore, in order to be practical and available to the general population, detection methods must be efficient enough to accommodate a large number of different samples.

A number of techniques that are more rapid but less comprehensive than direct sequencing have been developed for detecting nucleotide sequence variations. Many of these techniques are based on detecting differences, between normal and mutant nucleotide sequences, in hybridization (e.g., allele specific hybridization), secondary structure (e.g., single strand conformation polymorphism analysis, heteroduplex analysis), melting (constant denaturing gel electrophoresis, denaturing gradient gel electrophoresis), and susceptibility to cleavage (either chemical or restriction enzyme cleavage). Other techniques, such as the protein truncation test, detect changes on the protein level. For a summary of such techniques, see Marajver & Petty, 1996, Clinics in Lab. Med. 16: 139–167, especially Table 5 at p. 152.

Efforts have independently focused primarily on increasing the rapidity of processing sequencing analyses or increasing the comprehensiveness of the hybridization-based techniques. There remains a need, however, for a systematic method of detecting mutations in individual gene samples that is both accurate enough to provide a reliable diagnosis to an individual patient and efficient enough to be practical for application to the general population.

3. SUMMARY OF THE INVENTION

It is an object of the invention to provide a step-wise integrated process for efficient and accurate detection of variations in polynucleotide sequences. For the purpose of convenience, the steps are described herein according to the following categories of analysis: Stage I, Stage II, and Stage III. Stage I involves allele specific hybridization assays for detection of known mutations in the test gene sample. Stage II analysis involves sequence variation locating assays, with subsequent targeted confirmatory sequencing of detected sequence variations. Stage III analysis involves direct sequencing analysis of any regions of the polynucleotide not sequenced in Stage II.

Stages I, II, and III are components of an overall sequence variation detection process. In one embodiment of the invention, Stage I analysis is followed by Stage II analysis, then by Stage III analysis. In another embodiment of the invention, Stage I analysis is followed by Stage II analysis without proceeding on to Stage III. In yet another embodiment of the invention, Stage I analysis is followed by Stage III analysis. In still another embodiment of the invention, the process is initiated with Stage II analysis, followed by Stage III analysis.

4. BRIEF DESCRIPTION OF THE FIGURES

FIGS. 1A–1J. Nucleotide sequence and encoded amino acid sequence of the BRCA1$^{(omi1)}$ gene.

5. DETAILED DESCRIPTION OF THE INVENTION

Described below is a step-wise integrated process for efficient and accurate detection of variations in polynucleotide sequences. For the purpose of convenience, the steps are described herein according to the following categories of analysis: Stage I, Stage II, and Stage III.

The present invention can be used to identify sequence variations in any polynucleotide sequence. For example, the present invention can be used to detect mutations in any gene that plays a role in disease. Examples of genes which can be analyzed for mutations and other sequence variations in accordance with the invention include, but are not limited to, BRCA1, BRCA2, BRCA3, cystic fibrosis transmembrane regulator (CFTR), dystrophin, neurofibromatosis I (NFI), neurofibromatosis II (NFII), and p53. Reference sequences for known genes can be found, for example, by searching the world wide web site of GenBank at http://www.ncbi.nlm.nih.gov (for example, BRCA1 at accession #Y08757 (or FIG. 1, herein); BRCA2 at accession #U43746; dystrophin at locus HUMDYS; CFTR at accession #M28668; NF1 at accession #M89914, NF2 at accession #L27131; and p53 at accession #X54156).

The following definitions are provided for the purpose of understanding this invention.

"Coding sequence" or "DNA coding sequence" refers to those portions of a gene which, taken together, code for a peptide (protein), or which nucleic acid itself has function.

"BRCA1$^{(omi)}$" refers collectively to the "BRCA1$^{(omi1)}$", "BRCA1$^{(omi2)}$" and "BRCA1$^{(omi3)}$" coding sequences.

"BRCA1$^{(omi1)}$" refers to the most frequently occurring coding sequence for the BRCA1 gene. This coding sequence was found by end-to-end sequencing of BRCA1 alleles from individuals randomly drawn from a Caucasian population found to have no family history of breast or ovarian cancer. The sequenced gene was found not to contain any mutations. BRCA1$^{(omi1)}$ was determined to be a consensus sequence by calculating the frequency with which the coding sequence occurred among the sample alleles sequenced. BRCA1$^{(omi1)}$ is shown in FIG. 1.

"BRCA1$^{(omi2)}$" and "BRCA1$^{(omi3)}$" refer to two additional, less frequently occurring coding sequences for the BRCA1 gene which were also isolated from individuals randomly drawn from a Caucasian population found to have no family history of breast or ovarian cancer. The differences among BRCA1$^{(omi1)}$, BRCA1$^{(omi2)}$ and BRCA1$^{(omi3)}$ are summarized in Table 1, below.

"Primer" as used herein refers to a sequence comprising about 20 or more nucleotides of a gene.

A "target polynucleotide" refers to the nucleic acid sequence of interest e.g., the BRCA1 encoding polynucleotide.

"Consensus" means the most commonly occurring in the population.

"Substantially complementary to" refers to a probe or primer sequences which hybridize to the sequences provided under stringent conditions and/or sequences having sufficient homology with test polynucleotide sequences, such that the allele specific oligonucleotide probe or primers hybridize to the test polynucleotide sequences to which they are complimentary.

"Isolated" as used herein refers to substantially free of other nucleic acids, proteins, lipids, carbohydrates or other materials with which they may be associated. Such association is typically either in cellular material or in a synthesis medium.

"Sequence variation" as used herein refers to any difference in nucleotide sequence between two different oligonucleotide or polynucleotide sequences.

"Polymorphism" as used herein refers to a sequence variation in a gene which is not associated with known pathology.

"Mutation" as used herein refers to a sequence variation in a gene which results in the gene coding for a non-functioning protein or a protein with substantially reduced or altered function.

"Pre-determined sequence variation" as used herein refers to a nucleotide sequence that is designed to be different than the corresponding sequence in a reference nucleotide sequence. A pre-determined sequence variation can be a known mutation in a gene.

"Allele specific hybridization assay" as used herein refers to an assay to detect the presence or absence of a pre-determined sequence variation in a test polynucleotide or oligonucleotide by hybridizing the test polynucleotide or oligonucleotide with a polynucleotide or oligonucleotide of pre-determined sequence such that differential hybridization between matching nucleotide sequences versus nucleotide sequences containing a mismatch is detected.

"Sequence variation locating assay" as used herein refers to an assay that detects a sequence variation in a test polynucleotide or oligonucleotide and localizes the position of the sequence variation to a sub-region of the test polynucleotide, without necessarily determining the precise base change or position of the sequence variation.

"Targeted confirmatory sequencing" as used herein refers to sequencing a polynucleotide in the region wherein a sequence variation has been located by a sequence variation locating assay in order to determine the precise base change and/or position of the sequence variation.

The aforementioned three categories of analysis, Stage I, Stage II, and Stage III, are components of an overall sequence variation detection process. Stage I involves allele specific hybridization assays for detection of known mutations in the test gene sample. Stage II analysis involves sequence variation locating assays, with subsequent targeted confirmatory sequencing of detected sequence variations. Stage III analysis involves direct sequencing analysis of any regions of the polynucleotide not sequenced in Stage II. Stage I, II and III may be combined differently to identify sequence variations in any polynucleotide sequence. Stage I analysis may be followed by Stage II analysis, then by Stage III analysis. Stage I analysis may be followed by Stage II analysis without proceeding on to Stage III. Stage I analysis may be followed by Stage III analysis. The analysis may also be initiated with Stage II analysis, followed by Stage III analysis.

One embodiment of the present invention is a method for determining the presence or absence of a sequence variation in a gene sample, comprising:
 (a) performing an allele specific hybridization assay for the presence or absence of one or more pre-determined sequence variations;
 (b) if no pre-determined sequence variation is found in step (a), then performing a sequence variation locating assay;
 (c) if no sequence variation is found in step (b), then sequencing the gene sample; and
 (d) determining the presence or absence of a sequence variation by analyzing the sequences obtained in step (c) against a reference sequence.

The method may further comprise repeating the allele specific hybridization until a predetermined number of known sequence variations have been tested for. The allele specific hybridization may also comprise testing for a pre-determined number of sequence variations in a single step not requiring repetition. The predetermined sequence variation in step (a) may be a known mutation. The sequence variation may also be a known mutation. The allele specific hybridization assay may be performed using a dot blot format, a multiplex format, a reverse dot blot format, a MASDA format, or a chip array format. The sequence variation locating assay may be performed using a protein truncation assay, a chemical cleavage assay, a heteroduplex analysis, a single strand conformation polymorphism assay, a constant denaturing gel, electrophoresis assay, or a denaturing gradient gel electrophoresis assay. The sequencing of a gene sample may be performed in only the forward or reverse direction, or in both the forward and reverse directions. Both exons and introns of the gene or parts thereof may be sequenced. All exons and introns may also be sequenced from end to end. Alternatively, only exons or only intronic sequences may be sequenced. The reference sequence may be a coding sequence, a genomic sequence, or one or more exons of the gene. The present method may be used to identify sequence variations in any polynucleotide sequence. For example, the gene of interest may be a human BRCA1 gene. Accordingly, the reference sequence may be a BRCA1 coding sequence or a BRCA1 genomic sequence.

A further embodiment of the invention is a method for determining the presence or absence of a sequence variation in a gene sample, comprising:
  (a) performing an allele specific hybridization assay for the presence of one or more pre-determined sequence variations;
  (b) if no pre-determined sequence variation is found in step (a), then performing a sequence variation locating assay;
  (c) if a sequence variation is detected in step (b), then performing targeted confirmatory sequencing; and
  (d) determining the presence or absence of a sequence variation by analyzing the sequences obtained in step (c) against a reference sequence.

The method may further comprise repeating the allele specific hybridization until a predetermined number of known sequence variations have been tested for. The allele specific hybridization may also comprise testing for a pre-determined number of sequence variations in a single step not requiring repetition. The predetermined sequence variation in step (a) may be a known mutation. The sequence variation may also be a known mutation. The allele specific hybridization assay may be performed using a dot blot format, a multiplex format, a reverse dot blot format, a MASDA format, or a chip array format. The sequence variation locating assay may be performed using a protein truncation assay, a chemical cleavage assay, a heteroduplex analysis, a single strand conformation polymorphism assay, a constant denaturing gel, electrophoresis assay, or a denaturing gradient gel electrophoresis assay. The sequencing of a gene sample may be performed in only the forward or reverse direction, or in both the forward and reverse directions. Both exons and introns of the gene or parts thereof may be sequenced. All exons and introns may also be sequenced from end to end. Alternatively, only exons or only intronic sequences may be sequenced. The reference sequence may be a coding sequence, a genomic sequence, or one or more exons of the gene. The present method may be used to identify sequence variations in any polynucleotide sequence. For example, the gene of interest may be a human BRCA1 gene. Accordingly, the reference sequence may be a BRCA1 coding sequence or a BRCA1 genomic sequence.

A further embodiment of the invention is a method for determining the presence or absence of a sequence variation in a gene sample, comprising:
  (a) performing an allele specific hybridization assay for the presence or absence of one or more pre-determined sequence variations; and
  (b) if no pre-determined sequence variation is found in step (a), then sequencing the gene sample; and
  (c) determining the presence or absence of a sequence variation by analyzing the sequences obtained in step (b) against a reference sequence.

The method may further comprise repeating the allele specific hybridization until a predetermined number of known sequence variations have been tested for. The allele specific hybridization may also comprise testing for a pre-determined number of sequence variations in a single step not requiring repetition. The predetermined sequence variation in step (a) may be a known mutation. The sequence variation may also be a known mutation. The allele specific hybridization assay may be performed using a dot blot format, a multiplex format, a reverse dot blot format, a MASDA format, or a chip array format. The sequencing of a gene sample may be performed in only the forward or reverse direction, or in both the forward and reverse directions. Both exons and introns of the gene or parts thereof may be sequenced. All exons and introns may also be sequenced from end to end. Alternatively, only exons or only intronic sequences may be sequenced. The reference sequence may be a coding sequence, a genomic sequence, or one or more exons of the gene. The present method may be used to identify sequence variations in any polynucleotide sequence. For example, the gene of interest may be a human BRCA1 gene. Accordingly, the reference sequence may be a BRCA1 coding sequence or a BRCA1 genomic sequence.

A further embodiment of the invention is a method for determining the presence or absence of a sequence variation in a gene sample, comprising:
  (a) performing a sequence variation locating assay;
  (b) if no sequence variation is found in step (a), then sequencing the gene sample; and
  (c) determining the presence or absence of a sequence variation by analyzing the sequences obtained in step (b) against a reference sequence.

The sequence variation may be a known mutation. The sequence variation locating assay may be performed using a protein truncation assay, a chemical cleavage assay, a heteroduplex analysis, a single strand conformation polymorphism assay, a constant denaturing gel, electrophoresis assay, or a denaturing gradient gel electrophoresis assay. The sequencing of a gene sample may be performed in only the forward or reverse direction, or in both the forward and reverse directions. Both exons and introns of the gene or parts thereof may be sequenced. All exons and all introns may also be sequenced from end to end. Alternatively, only exons or only intronic sequences may be sequenced. The reference sequence may be a coding sequence, a genomic sequence, or one or more exons of the gene. The present method may be used to identify sequence variations in any polynucleotide sequence. For example, the gene of interest may be a human BRCA1 gene. Accordingly, the reference sequence may be a BRCA1 coding sequence or a BRCA1 genomic sequence.

5.1. STAGE I: DETECTION OF PRE-DETERMINED SEQUENCE VARIATIONS

Stage I analysis is used to determine the presence or absence of a pre-determined nucleotide sequence variation; preferably a known mutation or set of known mutations in the test gene. In accordance with the invention, such pre-determined sequence variations are detected by allele specific hybridization. An allele specific hybridization assay detects the differential ability of mismatched nucleotide sequences (e.g., normal:mutant) to hybridize with each other, as compared with matching (e.g., normal:normal or mutant:mutant) sequences.

5.1.1. DETECTION OF PRE-DETERMINED SEQUENCE VARIATIONS USING ALLELE SPECIFIC HYBRIDIZATION

A variety of methods well-known in the art can be used for detection of pre-determined sequence variations by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a sequence variation in the target sequence is indicated by hybridization between the oligonucleotide probe and the target fragment under conditions in which an oligonucleotide probe containing a normal sequence does not hybridize to the target fragment. A lack of hybridization between the sequence variant (e.g., mutant) oligonucleotide probe and the target polynucleotide fragment indicates the absence of the specific sequence variation (e.g., mutation) in the target fragment. In a preferred embodiment, the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, the experimental embodiment set forth in Mullis, K. B., 1987, U.S. Pat. No. 4,683,202). The use of such a dot blot format is described in detail in the example in section 6.1, below, detailing the Stage I analysis of the human BRCA1 gene to detect the presence or absence of eight different known mutations using eight corresponding ASOs.

Membrane-based formats that can be used as alternatives to the dot blot format for performing ASO analysis include, but are not limited to, reverse dot blot, multiplex format, and multiplex allele-specific diagnostic assay (MASDA).

In a reverse dot blot format, oligonucleotide or polynucleotide probes having known sequence are immobilized on the solid surface, and are subsequently hybridized with the labeled test polynucleotide sample.

In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 by A. P. Shuber, and in Michalowsky et al., October 1996, American Journal of Human Genetics 59(4): A272, poster 1573, each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case the mRNA is first reversed transcribed into cDNA and then amplified according to the well known technique of RT-PCR (see, for example, U.S. Pat. No. 5,561,058 by Gelfand et al.).

Alternative methods to the membrane-based methods described above include, but are not limited to, chip array hybridization. This method is described in detail in Hacia et al., 1996, Nature Genetics 14: 441–447, which is hereby incorporated by reference in its entirety. As described in Hacia et al., high density arrays of over 96,600 oligonucleotides, each 20 nucleotides in length, can be applied to a single glass or silicon chip. Each oligonucleotide can be designed to contain a pre-determined sequence that varies from the corresponding test gene sequence such that, collectively, the applied oligonucleotides contain small variations in the test gene sequence potentially spanning the entire test gene. The oligonucleotides applied to the chip, therefore, can contain pre-determined sequence variations that are not yet known to occur in the population, or they can be limited to mutations that are known to occur in the population. The immobilized oligonucleotides are then hybridized with a test polynucleotide sample. The hybridization pattern of the test polynucleotide sample is compared with that of the reference polynucleotide. Differences in hybridization can be localized to specific positions on the chip array containing individual oligonucleotides with pre-determined sequence variations.

In accordance with the invention, when no sequence variations are detected in a given test gene using the Stage I analysis described above, the presence of alternative sequence variations is subsequently tested by analyzing the test gene according Stage II, or Stage III, or Stage II followed by Stage III, as described in Sections 5.2 and 5.3, below.

5.2. STAGE II: SEQUENCE VARIATION LOCATING AND TARGETED CONFIRMATORY SEQUENCING

Test genes, such as those determined to contain none of the specific mutations tested in Stage I, can be further investigated for the presence of a variation in the nucleotide sequence of the test gene. According to Stage II analysis, a sequence variation locating assay is used to localize a sequence variation to a sub-region within the test polynucleotide. Such localization allows for subsequent targeted confirmatory sequencing to identify the specific sequence variation. In accordance with the invention, sequence variations can be located by initial detection at either the nucleic acid level (nucleotide sequence) or the protein level (amino acid sequence).

Stage II analysis can be used to identify sequence variations that represent mutations in the test gene. When no sequence variation is detected by Stage II analysis, or when the sequence variation is determined not to represent a mutation of the test gene, the test gene is subsequently subjected to Stage III analysis, as described in Section 5.3, below.

In a preferred embodiment of Stage II analysis, sequence variations that result in mutant polypeptides that are shorter than the corresponding normal polypeptide are initially detected at the protein level using a protein truncation assay.

5.2.1. PROTEIN TRUNCATION ASSAY

Mutations that cause a truncated protein product are detected by producing a protein product encoded by the test gene and analyzing its apparent molecular weight. A protein truncation assay provides the advantage of directly detecting nucleotide sequence variations that affect the encoded polypeptide, often in a dramatic fashion. Thus, in addition to localizing the site of the sequence variation for targeted nucleic acid sequencing, a protein truncation assay can provide immediate information of the effect of the sequence variation on the encoded protein.

Mutant truncated proteins can result from nonsense substitution mutations, frameshift mutations, in-frame deletions, and splice site mutations.

A nonsense substitution mutation occurs when a nucleotide substitution causes a codon that normally encodes an amino acid to code for one of the three stop signals (TGA, TTA, TAG). For such mutations, the protein truncation point occurs at the corresponding position in the gene at which the mutation occurs.

Frameshift mutations result from the addition or deletion of any number of bases that is not a multiple of three (e.g., one or two base insertion or deletion). For such frameshift mutations, the reading frame is altered from the point of mutation downstream. A stop codon, and resulting truncation of the corresponding encoded protein product, can occur at any point from the position of the mutation downstream.

In-frame deletions result from the deletion of one or more codons from the coding sequence. The resulting protein product lacks only those amino acids that were encoded by the deleted codons.

Splice site mutations result in an improper excision and/or joining of exons. These mutations can result in inclusion of some or all of an intron in the mRNA, or deletion of some or all of an exon from the mRNA. In some instances, these insertions or deletions result in stop codon being encountered prematurely, as typically occurs with frameshift mutations. In other instances, one or more specific exons is deleted from the mature mRNA in such a manner that the proper reading frame is maintained for the remaining exons, i.e., non-contiguous exons are fused in frame with each other. For such splice mutations, the encoded protein may terminate at the appropriate stop codon, but is shortened by the absence of the unspliced internal exon.

In a preferred embodiment, the length of the protein encoded by the test gene is analyzed by isolating all or a portion of the test gene for use as a template in an in vitro transcription/translation reaction. The template for transcription can be a cDNA copy of all or a portion of the gene. Using a cDNA template allows for translation initiation at the endogenous translation start site.

Alternatively, individual exons isolated from genomic DNA are tested separately. Such exons can be amplified using PCR from genomic DNA template. Since internal exons generally require a translation initiation signal (i.e., an ATG start codon), amplification primers are carefully selected such that the amplification product contains translation start signal in the proper reading frame through incorporation of the primer sequence into the amplification product.

In addition, particularly long cDNAs or individual exons that encode very large protein products can be divided into separate fragments. Each fragment can then serve individually as a separate template for transcription. Such fragments can be designed and generated by amplification using carefully chosen primers. In amplifying any fragment that does not contain a translation initiation signal (e.g., ATG) at its 5'-end, primers that incorporate such a signal at the 5'-end in frame with the coding sequence are used.

The translated protein products are then analyzed by well-known techniques for determining the apparent molecular weight of the polypeptide chains, such as SDS polyacrylamide gel electrophoresis (SDS/PAGE).

Some types of truncated protein products may be difficult to detect by such SDS/PAGE analysis. Extremely short truncated protein products may be too small to be detected on the gel. In addition, protein products that are only slightly truncated, i.e., by one or a few amino acids, may not be resolvable from the normal length protein product also present on the gel (derived from the normal allele amplification product template present in the in vitro transcription/translation reaction). Therefore, if no truncated protein products are detected, the terminal regions of the amplification products must be sequenced to ensure that extremely short and nearly full-length protein products are not encoded by the test polynucleotide sample. Preferably, even if a truncation product is detected, the terminal regions are sequenced to rule out the presence of additional upstream mutations.

In addition, if a slightly truncated protein results from a small internal deletion (e.g., a small in-frame deletion), not only will such a protein be difficult to resolve on the gel, the mutation will not be detected by sequencing the termini of the polynucleotide. Such mutations can be detected, however, in Stage III analysis, as described in Section 5.3, below.

The use of such a protein truncation assay is described in detail in the example in Section 6.2, below, for the detection of truncated human BRCA1 proteins resulting from mutations in exon 11 of the human BRCA1 gene. Furthermore, the detection of the C3508G mutation in the human BRCA1 gene using the protein truncation assay described in Section 6.2 is described in the example in Section 7, below.

5.2.2. ASSAYS FOR NUCLEOTIDE SEQUENCE VARIATIONS

A variety of methods, in addition to protein truncation assay, can be used to detect and locate a sequence variation within a region of a test gene, including but not limited to single strand conformation polymorphism (SSCP) analysis, heteroduplex analysis (HA), denaturing gradient gel electrophoresis (DGGE), constant denaturant gel electrophoresis (CDGE), and chemical cleavage analysis. Each of these techniques can be used alone or in conjunction with each other. In each case, once the nucleotide sequence variation is localized, the implicated region is sequenced to identify the exact variation in a process referred to herein as targeted confirmatory sequencing. The altered nucleotide sequence is then analyzed to determine its predicted effect on the encoded protein, e.g., whether the change results in a change in the amino acid sequence.

In single strand conformation polymorphism (SSCP) analysis, a double stranded PCR product is heated to melt the duplex and then run single stranded on a gel. For a general discussion of SSCP analysis, see Weber, 1996, supra. The single stranded DNA folds on itself in a characteristic fashion. Sequence variations between two amplified allelic sequences alter this conformation and change the migration on the gel, either more quickly or more slowly. When a shift with respect to the migration rate of the normal allele is detected on the gel, the "shifted" fragment is sequenced to identify the specific mutation.

Heteroduplex analysis (HA) can also be used to detect and localize sequence variations to a region within the test gene. HA is described in detail in Gayther, et al., 1996, Am. J. Hum. Genet. 58: 451–456. PCR products from individuals who are heterozygous for a mutation, when heated and then allowed to reanneal, form four types of products: two homoduplexes (one normal:normal, one mutant:mutant) and two heteroduplexes (normal:mutant of each strand). The homoduplexes and heteroduplexes will migrate at different rates in a non-denaturing gel. The fragment that is abnormal is sequenced to identify the specific mutation.

In denaturing gradient gel electrophoresis (DGGE), DNA duplexes start to melt at one end in a gel of an increasing denaturant. Mutations in the DNA alter the way it melts as it moves through the gel. Sequencing is performed on the fragment that is abnormal to detect the specific mutation. For more detail, see, for example, Fodde & Losekoot, 1994, Hum. Mutat. 3: 83–94; and Sheffield et al., 1989, Proc. Natl. Acad. Sci. USA 86: 232–236.

Constant denaturant gel electrophoresis (CDGE) is described in detail in Smith-Sorenson et al., 1993, Human Mutation 2: 274–285 (see also, Anderson & Borreson, 1995, Diagnostic Molecular Pathology 4: 203–211). A given DNA duplex melts in a predetermined, characteristic fashion in a gel of a constant denaturant. Mutations alter this movement. An abnormally migrating fragment is isolated and sequenced to determine the specific mutation.

Chemical cleavage analysis is described in U.S. Pat. No. 5,217,863, by R. G. H. Cotton. Like heteroduplex analysis, chemical cleavage detects different properties that result when mismatched allelic sequences hybridize with each other. Instead of detecting this difference as an altered migration rate on a gel, the difference is detected in altered susceptibility of the hybrid to chemical cleavage using, for example, hydroxylamine, or osmium tetroxide, followed by piperidine.

5.3. STAGE III: NUCLEOTIDE SEQUENCING ANALYSIS

In accordance with the invention, when no mutations are detected after analysis by Stage I, or Stage II, or Stage I followed by Stage II, the test gene is subjected to Stage III sequencing analysis. Stage III sequencing differs from the confirmatory sequencing of Stage II by not being targeted to a particular region of the gene proposed or known to contain a sequence variation. Thus, Stage III sequencing is used to detect sequence variations in the test polynucleotide (e.g., part or all of a gene) by directly sequencing the test polynucleotide and comparing its nucleotide sequence to a corresponding reference sequence (e.g., a normal sequence of the gene).

In one embodiment of the invention, Stage III sequencing analysis is performed by sequencing the entire gene including all introns and exons from end-to-end. In another embodiment, only exons (one or more) are sequenced. In yet another embodiment, only introns (one or more) are sequenced. In additional embodiments only portions of one or more introns, or portions of one or more exons, or combinations of partial or whole introns and partial or whole exons are sequenced.

Sequencing can be carried out only so far as a mutation is detected. Alternatively, sequencing can be continued to any point beyond the detection of a mutation up to and including the sequencing of every nucleotide in the entire gene, including each exon, intron, regulatory region, and other non-transcribed regions constituting a part of the functional gene.

The nucleotide sequence, in accordance with the invention, can be determined for just one of the DNA strands of the gene (e.g., "forward direction" sequencing, or sequencing the "sense" strand), or, preferably, by sequencing both strands (i.e., both forward/sense strands and reverse/antisense strands).

In a preferred embodiment for the human BRCA1 gene, each of the 22 coding exons is sequenced (exons 2, 3, 5, 5–24).

A number of methods well-known in the art can be used to carry out the sequencing reactions. Preferably, enzymatic sequencing based on the Sanger dideoxy method is used.

The sequencing reactions can be analyzed using methods well-known in the art, such as polyacrylamide gel electrophoresis. In a preferred embodiment for efficiently processing multiple samples, the sequencing reactions are carried out and analyzed using a fluorescent automated sequencing system such as the Applied Biosystems, Inc. ("ABI", Foster City, Calif.) system. For example, PCR products serving as templates are fluorescently labeled using the Taq Dye Terminator® Kit (Perkin-Elmer cat# 401628). Dideoxy DNA sequencing is performed in both forward and reverse directions on an ABI automated Model 377® sequencer. The resulting data can be analyzed using "Sequence Navigator®" software available through ABI.

Alternatively, large numbers of samples can be prepared for and analyzed by capillary electrophoresis, as described, for example, in Yeung et al., U.S. Pat. No. 5,498,324.

6. EXAMPLE 1

DETECTION OF SEQUENCE VARIATIONS IN POLYNUCLEOTIDES

The methods of the invention, which can be used to detect sequence variations in any polynucleotide sample, are demonstrated in the example set forth in this section, for the purpose of illustration, for one gene in particular, namely, the human BRCA1 gene. The BRCA1 gene is approximately 100,000 base pairs of genomic DNA encoding the 1836 amino acid BRCA1 protein. The sequence is divided into 24 separate exons. Exons 1 and 4 are noncoding, in that they are not part of the final functional BRCA1 protein product. Each exon consists of 200–400 bp, except for exon 11 which contains about 3600 bp (Weber, B., Science & Medicine (1996).

The consensus sequence for the coding region of the human BRCA1 gene, referred to herein as BRCA1$^{(omi1)}$ (SEQ ID NO:1, herein), was first disclosed in co-pending application Ser. No. 08/598,591 (as SEQ ID NO:1, therein), which is hereby incorporated by reference in its entirety. The BRCA1$^{(omi1)}$ is more highly represented in the population than the previously disclosed BRCA1 coding sequence available as GenBank Accession Number U14680. In particular, it has a different nucleotide at each of seven polymorphic positions in the gene. These polymorphisms are summarized in Table 1, below. In addition to the BRCA1$^{(omi1)}$ sequence, co-pending application Ser. No. 08/798,691, filed Feb. 12, 1997, describes the previously unknown BRCA1$^{(omi2)}$ SEQ ID NO.3 and BRCA1$^{(omi3)}$ alleles SEQ ID NO.3 of the BRCA1 gene which also differ from the U14680 sequence: BRCA1$^{(omi2)}$ SEQ ID NO.3 differs from the U14680 sequence at six of the seven polymorphic sites and differs from BRCA1$^{(omi1)}$ at only one of the seven polymorphic sites; BRCA1$^{(omi3)}$ differs from the U14680 sequence at one of the seven polymorphic sites (see Table 1, below). The BRCA1$^{(omi2)}$ SEQ ID NO.3 and BRCA1$^{(omi3)}$ SEQ ID NO.5 sequences are described as SEQ ID NOS: 3 and 5, respectively, in co-pending application Ser. No. 08/798,691.

The seven polymorphisms most commonly occurring in the population are summarized in Table 1, below.

TABLE 1

| | NUCLEOTIDE PRESENT AT EACH POLYMORPHIC POSITION IN BRCA1 CODING SEQUENCE | | | | | | |
|---|---|---|---|---|---|---|---|
| ALLELE | 2201 | 2430 | 2731 | 3232 | 3667 | 4427 | 4956 |
| BRCA1(omi1) (SEQ ID NO: 1) | T | C | T | G | G | C | G |
| BRCA1(omi3) (SEQ ID NO: 5) | T | C | T | G | G | T | G |
| BRCA1(omi2) (SEQ ID NO: 3) | C | T | T | A | A | T | A |
| U14680 | C | T | C | A | A | T | A |

6.1 ALLELE-SPECIFIC OLIGONUCLEOTIDE (ASO) ANALYSIS OF MUTATIONS IN THE BRCA1 GENE

6.1.1 Isolation of Genomic DNA

White blood cells were collected from the patient and genomic DNA was extracted from the white blood cells according to well-known methods (Sambrook, et al., Molecular Cloning, A Laboratory Manual, 2nd Ed., 1989, Cold Spring Harbor Laboratory Press, at 9.16–9.19).

6.1.2. PCR Amplification

The genomic DNA was used as a template to amplify a separate DNA fragment encompassing the site of each of the eight mutations to be tested. Each 50 µl PCR reaction contained the following components: 1 µl template (100 ng/µl) DNA, 5.0 µl 10×PCR Buffer (Perkin-Elmer), 5.0 µl dNTP (2 mM each dATP, dCTP, dGTP, dTTP), 5.0 µl Forward Primer (10 µmM), 5.0 µl Reverse Primer (10 mM), 0.5 µl Taq DNA Polymerase (Perkin-Elmer). 25 mM $MgCl_2$ was added to each reaction according to Table 2, below, and $H_2O$ was added to 50 µl. All reagents for each exon except the genomic DNA can be combined in a master mix and aliquoted into the reaction tubes as a pooled mixture.

| Temperature | Time | Number of Cycles |
|---|---|---|
| 95° C. | 5 minutes | 1 cycle |
| 95° C. | 30 seconds | |
| 55° C. | 30 seconds | 30 cycles |
| 72° C. | 1 minute | |
| 72° C. | 5 minutes | 1 cycle |
| 4° C. | infinity | 1 cycle |

Quality control agarose gel of PCR amplification:

The quality of the PCR products were examined prior to further analysis by electrophoresing an aliquot of each PCR reaction sample on an agarose gel. 5 µl of each PCR reaction was run on an agarose gel along side a DNA mass ladder (Gibco BRL Low DNA Mass Ladder, cat# 10068-013). The electrophoresed PCR products were analyzed according to the following criteria:

Each patient sample must show a single band of the corresponding size indicated in Table 2. If a patient sample demonstrates smearing or multiple bands, the PCR reaction must be repeated until a clean, single band is detected. The only exceptions to this are for the mutations 1294del40 and T>Gins59. If a patient sample from one of these two exons (11B and 6, respectively) demonstrates two bands instead of one, it may indicate the presence of the mutation. The 1294del40 mutation shortens the size of the corresponding PCR product by 40 bp and the T>Gins59 mutation lengthens the size of the corresponding PCR product by 59 bp. Patients heterozygous for these mutations would have a normal sized PCR product from the normal allele, and an altered sized PCR product from the mutant allele.

If no PCR product is visible or if only a weak band is visible, but the control reactions with placental DNA

TABLE 2

| BRCA1 Exon | Mutation | Primer Sequence (5'–3') | $Mg^{++}$ (mM) | Vol of 25 mM $Mg^{++}$ | Product Size (bp) | Seq. ID No. |
|---|---|---|---|---|---|---|
| 2 | 185delAG | 2F: GAA GTT GTC ATT TTA TAA ACC TTT | 1.6 | 3.2 | 258 | 73 |
| | | 2R: TGT CTT TTC TTC CCT AGT ATG | | | | 74 |
| S | T300G | 5F: CTC TTA AGG GCA GTT GTG AG | 1.2 | 2.4 | 235 | 75 |
| | | 5R: TTC CTA CTG TGG TTG CTT CC | | | | 76 |
| 6 | T > G | 6F1: TTT CTA CTG TTG CTG CAT CT | 1.4 | 2.8 | 272 | 77 |
| | | 6R1: TAA TGT GCA AAC TTC CTG AG | | | | 78 |
| 11B | ll36insA | 11BF: TTA CTC ACT AAA GAC AGA ATG | 1.2 | 2.4 | 401 | 79 |
| | | 11BR: CCA GAA TAT TCA TCT ACC TCA | | | | 80 |
| 11B | 1294del40 | 11BF: TTA CTC ACT AAA GAC AGA ATG | 1.2 | 2.4 | 401 | 81 |
| | | 11BR: CCA GAA TAT TCA TCT ACC TCA | | | | 82 |
| 11L | 4184del4 | 11LF-1: GTA ATA TTG GCA AAG GCA TCT | 1.2 | 2.4 | 360 | 83 |
| | | 11LR: TAA AAT GTG CTC CCC AAA AGC A | | | | 84 |
| 13 | C4446T | 13F: AAT GGA AAG CTT CTC AAA GTA | 1.2 | 2.4 | 320 | 85 |
| | | 13R: ATG TTG GAG CTA GGT CTT TAC | | | | 86 |
| 20 | S3B2insC | 20F: ATA TGA CGT GTC TGC TCC AC | 1.2 | 2.4 | 399 | 87 |
| | | 20R: GGG AAT CCA AAT TAC ACA GC | | | | 88 |

For each exon analyzed for this mutation, the following control PCRs were set up:

(1) "Negative" DNA control (100 ng placental DNA (Oncor, Inc., Gaithersburg, Md.)

(2) Three "no template" controls

PCR for all exons was performed using the following thermocycling conditions:

template produced a clear band, the patient sample should be re-amplified with 2× as much template DNA.

All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

The optimum amount of PCR product on the gel should be 50–100 ng, which can be determined by comparing the intensity of the patient sample PCR products with that of the DNA mass ladder. If the patient sample PCR products contain less than 50–100 ng, the PCR reaction should be repeated until sufficient quantity is obtained.

6.1.3. Binding PCR Products to Nylon Membrane

A. The PCR products were denatured no more than 30 minutes prior to binding the PCR products to the nylon membrane. To denature the PCR products, the remaining PCR reaction (45 µl) and the appropriate positive control mutant gene amplification product were diluted to 200 ul final volume with PCR Diluent Solution (500 mM NaOH, 2.0 M NaCl, 25 mM EDTA) and mixed thoroughly. The mixture was heated to 95° C. for 5 minutes, and immediately placed on ice and held on ice until loaded onto dot blotter, as described below.

The PCR products were bound to 9 cm by 12 cm nylon Zeta Probe Blotting Membrane (Bio-Rad, Hercules, Calif., catalog number 162-0153) using a Bio-Rad dot blotter apparatus. Forceps and gloves were used at all times throughout the ASO analysis to manipulate the membrane, with care taken never to touch the surface of the membrane with bare hands.

3MM filter paper [Whatman®, Clifton, N.J.] and nylon membrane were pre-wet in 10×SSC from 20×SSC buffer stock (Appligene, France, catalog #130431), making sure the nylon membrane was wet thoroughly. The vacuum apparatus was rinsed thoroughly with dH$_2$O prior to applying the membrane. 100 µl of each denatured PCR product sample was added to the wells of the blotting apparatus. Each row of the blotting apparatus contained a set of reactions for a single exon to be tested, including a placental DNA (negative) control, a positive control, and three no template DNA controls. Information on the positive controls is listed in Table 3, below. Plasmid clones and PCR products were obtained from individual patients, and are interchangeable with synthetic oligonucleotides containing the respective mutant sequence.

TABLE 3

| Exon | Mutation | Description |
|------|----------|-------------|
| 2 | 185delAG | plasmid DNA |
| 5 | T300G | PCR product |
| 6 | T>Gins 59bp | synthetic oligo |
| 11B | 1136insA | PCR product |
| 11B | 1294del40 | PCR product |
| 11L | 4184del4 | synthetic oligo |
| 13 | C4446T | PCR product |
| 20 | 5382insC | PCR product |

When all liquid was suctioned through, the nylon membrane was placed on a piece of dry 3MM filter paper to prepare for fixing the DNA to the membrane.

The nylon filter was placed DNA side up on a piece of 3MM filter paper saturated with denaturing solution (1.5M NaCl, 0.5 M NaOH) for 5 minutes. The membrane was transferred to a piece of 3MM filter paper saturated with neutralizing solution (1M Tris-HCl, pH 8, 1.5 M NaCl) for 5 minutes. The neutralized membrane was then transferred to a dry 3MM filter DNA side up, and exposed to ultraviolet light (Stralinker, Stratagene, La Jolla, Calif.) for exactly 45 seconds. Shorter exposure time can result in the DNA not binding to the filter, and longer exposure time can result in degradation of the DNA. This UV crosslinking should be performed within 30 min. of the denaturation/neutralization steps. The nylon membrane was then cut into strips such that each strip contained a single row of blots of one set of reactions for a single exon.

6.1.4. Hybridizing Labeled oligonucleotides to the Nylon Membrane 6.1.4.1. Prehybridization The eight strips were prehybridized using the Hybaid® (Savant Instruments, Inc., Holbrook, N.Y.) hybridization apparatus and bottles. The Hybaid® bottles, each containing approximately 2ml of 2×SSC, were preheated to 52° C. in the Hybaid® oven. For each nylon strip, a single piece of nylon mesh cut slightly larger than the nylon membrane strip (approximately 1"×5") was pre-wet with 2×SSC. Each single nylon membrane was removed from the prehybridization solution and placed on top of the nylon mesh. The membrane/mesh "sandwich" was then transferred onto a piece of parafilm. The membrane/mesh sandwich was rolled lengthwise and place into the appropriate Hybaid® bottle, such that the rotary action of the Hybaid® apparatus caused the membrane to unroll. The bottle was capped and gently rolled to cause the membrane/mesh to unroll and to evenly distribute the 2×SSC, making sure that no air bubbles formed between the membrane and mesh or between the mesh and the side of the bottle. The 2×SSC was discarded and replaced with 5 mls TMAC Hybridization Solution, which contained 3 M TMAC (Sigma T-3411), 100 mM Na$_3$PO$_4$(pH6.8), 1 mM EDTA, 5×Denhardt's (1% Ficoll, 1% polyvinylpyrrolidone, 1% BSA (fraction V)), 0.6% SDS, and 100 ug/ml Herring Sperm DNA. The filter strips were prehybridized at 52° C. with medium rotation (approx. 8.5 setting on the Hybaid® speed control) for at least one hour. Prehybridization can also be performed overnight.

6.1.4.2. Labeling Oligonucleotides

The DNA sequences of the oligonucleotide probes used to detect the eight BRCA1 mutations were as follows (for each mutation, a mutant and a normal oligonucleotide must be labeled):

BRCA1 ASOs

| | Sequence | Seq. ID No. |
|---|---|---|
| 185delAG-Mutant | 5'-ATC TTA GTG TCC CAA AT-3' | 89 |
| 185delAG-Normal | 5'-AAT CTT AGA GTG TCC CA-3' | 90 |
| T300G-Mutant | 5'-CTT CAC AGG GTC CTT TA-3' | 91 |
| T300G-Normal | 5'-CTT CAC AGT GTC CTT TA-3' | 92 |
| T > G-Mutant | 5'-TCA AAC AAG TTA ATT TC-3' | 93 |
| T > G-Normal | 5'-TCA AAC ATT TTA ATT TC-3' | 94 |
| 1136insA-Mutant | 5'-CAG AAA AAA AAG GTA GA-3' | 95 |
| 1136insA-Normal | 5'-CAG AAA AAA AGG TAG AT-3' | 96 |
| 1294del40-Mutant | 5'-GTG ATG AAC AAA TGC CA-3' | 97 |
| 1294delL40-Normal | 5'-GAT GAC TCA CAT GAT GC-3' | 98 |
| 4184del4-Mutant | 5'-AGA AAA TAA GAA GAG CA-3' | 99 |
| 4184del4-Normal | 5'-AGA AAA TAA TCA AGA AG-3' | 100 |
| C4446T-Mutant | 5'-AGG ACC TGT GAA ATC CA-3' | 101 |
| C4446T-Normal | 5'-AGG ACC TGC GAA ATC CA-3' | 102 |
| 5382insC-Mutant | 5'-AGA GAA TCC CCA GGA CA-3' | 103 |
| 5382insC-Normal | 5'-AGA GAA TCC CAG GAC AG-3' | 104 |

Each labeling reaction contained 2 µl 5×Kinase buffer (or 1 µl of 10×kinase buffer), 5 µl gamma-ATP-$^{32}$P (not more than one week old), 1 µl T4 polynucleotide kinase, 3 µl oligonucleotide (20 µM stock), sterile H$_2$O to 10 µl final volume if necessary. The reactions were incubated at 37° C. for 30 minutes, then at 65° C. for 10 minutes to heat inactivate the kinase. The kinase reaction was diluted with an equal volume of sterile dH$_2$O (10 µl). The labeled oligonucleotides were stored at −20° C. until ready for use, but not for more than 21 days.

The oligos were purified on STE Micro Select-D, G-25 spin columns (catalog no. 5303-356769), according to the manufacturer's instructions. The 20 μl eluate was diluted into 80 μl dH$_2$O. The amount of radioactivity in the oligo sample was determined by measuring the radioactive counts per minute (cpm) in Probe Count. The total radioactivity must be at least 2 million cpm. For any samples containing less than 2 million total, the labeling reaction was repeated.

6.1.4.3. Hybridization with Mutant Oligonucleotides

2–5 million counts of each labeled mutant oligo probe was diluted into 5 mls of TMAC hybridization solution. 40 μl of 20 μM stock of unlabeled normal oligo was added to each tube containing probe and TMAC as an additional blocking reagent. Each probe mix was preheated to 52° C. in the hybridization oven. The prehybridization solution was removed from each bottle and replaced with the probe mix, making sure that no air bubbles formed as with the prehybridization. The filters were hybridized for 1 hour at 52° C. with moderate rotation rotation (approx. 8.5-setting on the Hybaid® speed control). Following hybridization, the probe mix was decanted into a storage tube and stored at 20° C. Each filter was rinsed by adding approximately 20 mls of 2×SSC+0.1% SDS at room temperature and rolling the capped bottle gently for approximately 30 seconds and pouring off the rinse. At this point, all filters, except those for mutants 1249del40 and 876delAG can be pooled and washed together in the same container. Each filter, including those for mutants 1249del40 and 876delAG, were washed with 2×SSC+0.1% SDS at room temperature for 20 minutes, with shaking. The filters for mutants 1249del40 and 876delAG should not be removed from the hybridization bottle. After the initial room temperature wash another 20 mls of wash buffer was added to the bottle. The 8763delAG filter was washed at 52° C. for 10 minutes. The 1294del40 filter was washed at 52° C. for 20 minutes.

The eight separate strips were placed on 2 pieces of pre-cut Whatman paper and covered with plastic wrap. The efficiency of the hybridization was tested using a survey meter. The strips were autoradiographed at −80 using Kodak Biomax MS film in a cassette containing a biomax intensifying screen.

6.1.4.3. Control Hybridization with Normal Oligonucleotides

The purpose of this step is to ensure that the PCR products were all transferred efficiently to the nylon membrane. In other words, this step ensures that any samples that do not yield a hybridization signal with the mutant oligonucleotides are truly negative for the mutation, rather than false negatives resulting from poor transfer of the PCR products to the membrane.

Following hybridization with the mutant oligonucleotides, as described in Section 6.1.4.2, above, each nylon membrane was washed in 2×SSC, 0.1% SDS for 20 minutes at 65° C. to strip off the mutant oligos. All eight nylon strips were prehybridized together in 35 mls of TMAC hybridization solution for at least 1 hour at 52° C. in a shaking water bath. 2–5 million counts of each of the normal labeled oligo probes plus 40 μl of 20 μM stock of unlabeled normal oligo were added directly to the container containing the nylon membranes and the prehybridization solution. The filters and probes were hybridized at 52° C. with shaking for at least 1 hour. Hybridization can be performed overnight. The hybridization solution was poured off; the nylon membrane was rinsed in 2×SSC, 0.1% SDS for 1 minute with gentle swirling by hand. The rinse was poured off and the membrane was washed in 2×SSC, 0.1% SDS at room temperature for 20 minutes with shaking.

The nylon membranes were removed and allowed to air dry for a few minutes, taking care not to let the nylon membranes dry completely. The nylon membranes were wrapped in one layer of plastic wrap and place on autoradiography film, as described in Section 6.1.2.4, above, except that exposure was for at least 1 hour.

For each sample, adequate transfer to the membrane is indicated by a strong autoradiographic hybridization signal. For each sample, an absence or weak signal when hybridized with its normal oligonucleotide, indicates an unsuccessful transfer of PCR product did not transfer successfully, and it is a false negative. The ASO analysis experiment must be repeated for any sample that did not successfully transfer to the nylon membrane.

6.1.5. Interpreting Results

After hybridizing with mutant oligos, the results for each exon are interpreted as follows:

TABLE 4A

| Result | Interpretation | Action |
|---|---|---|
|  | All controls indicate assay was successful | Record results — dark circles are mutation positive, and all others are negative |
|  | Assay not specific — mutant oligo hybridizing to normal DNA | Rewash membrane 30 minutes longer at appropriate temp. and re-expose |
|  | Mutant oligo probe was either washed off or did not label well enough, or PCR product was not transferred to membrane efficiently | Rehyb. with remaining labeled oligo. If still no signal, perform normal oligo hyb. as per section 6.1.4.3. to test transfer of PCR to membrane |

TABLE 4A-continued

| Result | | | | | Interpretation | Action |
|---|---|---|---|---|---|---|
| ● (+) | ○ (−) | ▨ NT | ▨ NT | ▨ NT | Positive and negative controls indicate assay was successful, but PCR is contaminated | Perform standard clean up procedures for PCR contamination |

After hybridization with normal oligos, interpret the results as follows:

TABLE 4B

| Result | | | | | Interpretation | Action |
|---|---|---|---|---|---|---|
| ● (+) | ● (−) | ○ NT | ○ NT | ○ NT | Results indicate transfer of PCR products to membrane was successful. | Record results. |
| ● (+) | ● (−) | ▨ #1 | ○ NT | ○ NT | Results indicate transfer of patient sample #1 was inefficient. May get false negative from this sample. | This sample will have to be transferred to another membrane and the assay repeated. |

6.2. PROTEIN TRUNCATION ASSAY

6.2.1. Amplification of Exon 11 from Genomic DNA

Exon 11 of the BRCA1 gene is approximately 3.4 kb long, and thus contains approximately 61% of the entire BRCA1 coding region. Three overlapping segments encompassing all of exon 11 were amplified directly from genomic DNA, isolated as described in Section 6.1.1, above. Fragment 1 encodes a 70.5 kD protein fragment, fragment 2 encodes a 74.8 kD protein fragment, and fragment 3 encodes a 41.5 kD protein fragment. The primers used for amplification are listed in Table 5 below. The ATG start codon that provided the translation initiation signal for each fragment is underlined.

6.2.2. In Vitro Transcription/Translation

The PCR amplification products were translated using the Tnt Coupled Reticulocyte Lysate System from Promega (cat #L4610). $^{35}$S-methionine from Amersham International (cat #SJ1015) was used to label the translation products. This particular "translation grade" methionine contains a stabilizer that retards the degradation of the $^{35}$S, and was not used more than 4 weeks after arrival. RNase inhibitor (Boehringer Mannheim—cat #799017) was added to the reactions.

Each 25 μl sample contained 12.5 μl rabbit reticulocyte extract, 1.0 μl TnT reaction buffer, 0.5 μl TnT T7 RNA polymerase, 0.5 μl 1 mM amino acid mixture minus methionine, 0.5 μl RNase inhibitor, 2.0 μl S-35 Methionine (1 mCi/100 μl), 500–750 ng DNA template, and deionized H$_2$O to 25 μl.

TABLE 5

| Primer | Sequence | Nucleotide Position In BRCA1 Coding Sequence | PCR Product Size (bp) | Protein Size (kD) | Seq. ID No. |
|---|---|---|---|---|---|
| | | Fragment 1 | | | |
| (11)F-1 (forward) | 5'-GCT AAT ACG ACT CAC TAT AGG AAC AGA CCA CC<u>ATG</u>G/CTT GTG AAT TTT CTG AGA CGG-3' | 793–813 | 1903 | 70.5 | 105 |
| (11)R-1B (reverse) | 5'-ATT CTG CAA ATA CTG AGC ATC A-3' | 2675–2696 | | | 106 |
| | | Fragment 2 | | | |
| (11)F-2 (forward) | 5'-GCT AAT ACG ACT CAC TAT AGG AAC AGA CCA CC<u>ATG</u>G/ACA ATT CAA AAG CAC CTA AAA AG-3' | 1921–1943 | 2022 | 74.8 | 107 |
| (11)R-2B (reverse) | 5'-ATT ACC TGG TTA CTG CAG TCA-3' | 3923–3943 | | | 108 |
| | | Fragment 3 | | | |
| (11)F-3 (forward) | 5'-GCT AAT ACG ACT CAC TAT AGG AAC AGA CCA CC<u>ATG</u>G/CAC CAC TTT TTC CCA TCA AGT C-3' | 3061–3082 | 1122 | 41.5 | 109 |
| (11)R-3 (reverse) | 5'-TTA TTT TCT TCC AAG CCC GTT CC-3' | 4161–4183 | | | 110 |

The reaction was incubated at 30° C. for 1 hour and 30 minutes, making sure that the temperature did not exceed 30° C.

6.2.3. Gel Analysis

The patient samples are compared to the corresponding fragments from a normal gene by SDS PAGE analysis. Truncated proteins are possible at any point in the sequence. Areas in the sequence where a mutation can occur that are difficult to detect because of small molecular weight or a stop signal occurring at the end of the sequence are accounted for by two methods. First, 288 base pairs of the 5' end of exon 11 fragment 1 are sequenced. This assures detectability of proteins 10 kD or less by means of sequencing and detectablity of proteins greater than 10 kD by means of protein truncation. A stop occurring at the end of exon 11 fragment 3 is identified by sequencing the final 257 base pairs of exon 11. Second, the areas between fragments one and two and two and three overlap each other by at least 27 kD.

The truncated protein should be of equal intensity on the gel as the normal fragment. When a potential truncated band is identified, the protein must be sized using the S-35 radiolabelled marker. For example, if a band appears on the gel from fragment 3 (in addition to the normal 43 kD band), then the sample is positive for a protein truncation. In order to identify the exact mutation causing the truncation, the size of the truncated protein is estimated from the size ladder on the gel autoradiograph. The position of the stop signal does not always indicate the position where the mutation occurred. Using the conversion factor, 270 bp=10 kD, convert the molecular weight into base pairs. Refer to the breakdown sequence of exon 11 to locate the region needed to be sequenced for the mutation. Once this calculation is performed, the particular region of exon 11 in which the mutation is predicted to lie is sequenced according to the standard sequencing procedure (see Section 6.3 below).

6.3. NUCLEOTIDE SEQUENCING ANALYSIS 6.3.1. PCR Amplification

Genomic DNA (100 nanograms) extracted from white blood cells of the patient, as described in Section 6.1.1, above. Each sample was amplified in a final volume of 25 microliters containing 1 microliter (100 nanograms) genomic DNA, 2.5 microliters 10×PCR buffer (100 mM Tris, pH 8.3, 500 mM KCl, 1.2 mM $MgCl_2$), 2.5 microliters 10×dNTP mix (2 mM each nucleotide), 2.5 microliters forward primer, 2.5 microliters reverse primer, and 1 microliter Taq polymerase (5 units), and 13 microliters of water.

The primers in Table 6, below were used to carry out amplification of the various sections of the BRCA1 gene samples. The primers were synthesized on an DNA/RNA Model 394® Synthesizer.

TABLE 6

BRCA1 PRIMERS AND SEQUENCING DATA

| EXON | | SEQUENCE | | | | SEQ. ID NO. | MER | MG++ | SIZE |
|---|---|---|---|---|---|---|---|---|---|
| EXON 2 | 2F | 5'GAA GTT | GTC | ATT TTA TAA ACC TTT-3' | | 7 | 24 | 1.6 | ~275 |
| | 2R | 5'TGT CTT | TTCTTC | CCT AGT ATG T-3' | | 8 | 22 | | |
| EXON 3 | 3F | 5'TCC TGA | CAC | AGC AGA CAT TTA-3' | | 9 | 21 | 1.4 | ~375 |
| | 3R | 5'TTG GAT | TTT | CGT TCT CAC TTA-3' | | 10 | 21 | | |
| EXON 5 | 5F | 5'CTC TTAAGG GCA | | GTT GTG AG-3' | | 11 | 20 | 1.2 | ~275 |
| | 5R | 5'TTCCTA CTG TGG | | TTG CTT CC | | 12 | 20 | 1 | |
| EXON 6 | 6/7F | 5'CTTATT TTAGTG | | TCC TTA AAA GG-3' | | 13 | 23 | 1.6 | ~250 |
| | 6R | 5'TTTCAT GGA CAG | | CAC TTG AGT G-3' | | 14 | 22 | | |
| EXON 7 | 7F | 5'CAC AAC | AAA | GAG CAT ACA TAG GG-3' | | 15 | 23 | 1.6 | ~275 |
| | 6/7R | 5'TCG GGT | TCA | CTC TGT AGA AG-3' | | 16 | 20 | | |
| EXON 8 | 8F1 | 5'TTCTCT TCA GGA | | GGA AAA GCA-3' | | 17 | 21 | 1.2 | ~270 |
| | 8R1 | 5'GCT GCC | TAC | CAC AAA TAC AAA-3' | | 18 | 21 | | |
| EXON 9 | 9F | 5'CCA CAG | TAG | ATG CTC AGT AAATA-3' | | 19 | 23 | 1.2 | ~250 |
| | 9R | 5'TAG GAA | AAT | ACC AGC TTCATA GA-3' | | 20 | 23 | | |
| EXON 10 | 10F | 5'TGG TCA | GCT | TTC TGT AAT CG-3' | | 21 | 20 | 1.6 | ~250 |
| | 10R | 5'GTA TCTACC CAC | | TCT CTT CTT CAG-3' | | 22 | 24 | | |
| EXON 11A | 11AF | 5'CCA CCT | CCA | AGG TGT ATC A-3' | | 23 | 19 | 1.2 | 372 |
| | 11AR | 5'TGT TATGTT GGC | | TCC TTG CT-3' | | 24 | 20 | | |
| EXON 11B | 11BF1 | 5'CAC TAA | AGA | CAG AAT GGA TCT A-3; | | 25 | 21 | 1.2 | ~400 |
| | 11BR1 | 5'GAA GAA | CCA | GAA TAT TCA TCT A-3' | | 26 | 21 | | |
| EXON 11C | 11CF1 | 5'TGA TGG | GGA | GTC TGA ATC AA-3' | | 27 | 20 | 1.2 | ~400 |
| | 11CR1 | 5'TCTGCT TTCTTG | | ATA AAA TCC T-3' | | 28 | 22 | | |
| EXON 11D | 11DF1 | 5'AGC GTC | CCC | TCA CAA ATA AA-3' | | 29 | 20 | 1.2 | ~400 |
| | 11DR1 | 5'TCA AGC | GCA | TGA ATA TGC CT-3' | | 30 | 20 | | |
| EXON 11E | 11EF | 5'GTA TAA | GCA | ATA TGG AAC TCG A-3' | | 31 | 22 | 1.2 | 388 |
| | 11ER | 5'TTAAGT TCA CTG | | GTA TTT GAA CA-3' | | 32 | 23 | | |
| EXON 11F | 11FF | 5'GAC AGC | GAT | ACT TTC CCA GA-3' | | 33 | 20 | 1.2 | 382 |
| | 11FR | 5'TGG AAC | AAC | CAT GAA TTAGTC-3' | | 34 | 21 | | |

TABLE 6-continued

BRCA1 PRIMERS AND SEQUENCING DATA

| EXON | | SEQUENCE | | | | SEQ. ID NO. | MER | MG++ | SIZE |
|---|---|---|---|---|---|---|---|---|---|
| EXON 11G | 11GF | 5'GGA AGT | TAG | CAC TCT AGG GA-3' | | 35 | 20 | 1.2 | 423 |
| | 11GR | 5'GCA GTG | ATA | TTA ACT GTC TGT A-3' | | 36 | 22 | | |
| EXON 11H | 11HF | 5'TGG GTC | CTT | AAA GAA ACA AAGT-3' | | 37 | 22 | 1.2 | 366 |
| | 11HR | 5'TCA GGT | GAC | ATT GAA TCTTCC-3' | | 38 | 21 | | |
| EXON 11I | 11IF | 5'CCA CTTTTTCCC | | ATC AAG TCA-3' | | 39 | 21 | 1.2 | 377 |
| | 11IR | 5'TCA GGA | TGC | TTA CAA TTACTT C-3' | | 40 | 21 | | |
| EXON 11J | 11JF | 5'CAA AAT | TGA | ATG CTA TGC TTA GA-3' | | 41 | 23 | 1.2 | 377 |
| | 11JR | 5'TCG GTA | ACC | CTG AGC CAA AT-3' | | 42 | 20 | | |
| EXON 11K | 11KF | 5'GCA AAAGCG TCC | | AGA AAG GA-3' | | 43 | 20 | 1.2 | 396 |
| | 11KR-1 | 5'TATTTG CAG | TCA | AGT CTT CCA A-3' | | 44 | 22 | | |
| EXON 11L | 11LF-1 | 5'GTA ATA | TTG | GCA AAG GCA TCT-3' | | 45 | 22 | 1.2 | 360 |
| | 11LR | 5'TAA AAT | GTG | CTC CCC AAA AGC A-3' | | 46 | 22 | | |
| EXON 12 | 12F | 5'GTC CTG | CCA | ATG AGA AGA AA-3' | | 47 | 20 | 1.2 | ~300 |
| | 12R | 5'TGT CAG | CAA | ACC TAA GAA TGT-3' | | 48 | 21 | | |
| EXON 13 | 13F | 5'AAT GGA | AAG | CTT CTC AAAGTA-3' | | 49 | 21 | 1.2 | ~325 |
| | 13R | 5'ATG TTG | GAG | CTA GGT CCT TAC-3' | | 50 | 21 | | |
| EXON 14 | 14F | 5'CTA ACC | TGA | ATT ATC ACT ATC A-3' | | 51 | 22 | 1.2 | ~310 |
| | 14R | 5'GTG TATAAATGC | | CTG TAT GCA-3' | | 52 | 21 | | |
| EXON 15 | 15F | 5'TGG CTG | CCC | AGG AAG TATG-3' | | 53 | 19 | 1.2 | ~375 |
| | 15R | 5'AAC CAG | AAT | ATC TTT ATG TAG GA-3' | | 54 | 23 | | |
| EXON 16 | 16F | 5'AAT TCTTAA CAG | | AGA CCA GAA C-3' | | 55 | 22 | 1.6 | ~550 |
| | 16R | 5'AAA ACT | CTT | TCC AGA ATG TTG T-3' | | 56 | 22 | | |
| EXON 17 | 17F | 5'GTG TAG | AAC | GTG CAG GAT TG-3' | | 57 | 20 | 1.2 | ~275 |
| | 17R | 5'TCG CCT | CAT | GTG GTT TTA-3' | | 58 | 18 | | |
| EXON 18 | 18F | 5'GGC TCTTTAGCT | | TCT TAG GAC-3' | | 59 | 21 | 1.2 | ~350 |
| | 18R | 5'GAG ACC | ATT | TTC CCA GCA TC-3' | | 60 | 20 | | |
| EXON 19 | 19F | 5'CTG TCA | TTC | TTC CTG TGC TC-3' | | 61 | 20 | 1.2 | ~250 |
| | 19R | 5'CAT TGT | TAA | GGA AAG TGG TGC-3' | | 62 | 21 | | |
| EXON 20 | 20F | 5'ATA TGA | CGT | GTC TGC TCC AC-3' | | 63 | 20 | 1.2 | ~425 |
| | 20R | 5'GGG AAT | CCA | AAT TAC ACA GC-3' | | 64 | 20 | | |
| EXON 21 | 21F | 5'AAG CTC | TTC | CTT TTT GAA AGT C-3' | | 65 | 22 | 1.6 | ~300 |
| | 21R | 5'GTA GAG | AAA | TAG AAT AGC CTC T-3' | | 66 | 22 | | |
| EXON 22 | 22F | 5'TCC CAT | TGA | GAG GTC TTG CT-3' | | 67 | 20 | 1.6 | ~300 |
| | 22R | 5'GAG AAG | ACT | TCT GAG GCT AC-3' | | 68 | 20 | | |
| EXON 23 | 23F-1 | 5'TGA AGT | GAC | AGT TCC AGT AGT-3' | | 69 | 21 | 1.2 | ~250 |
| | 23R-1 | 5'CAT TTTAGC | CAT | TCA TTC AAC AA-3' | | 70 | 23 | | |
| EXON 24 | 24F | 5'ATG AAT | TGA | CAC TAA TCTCTG C-3' | | 71 | 22 | 1.4 | ~285 |
| | 24R | 5'GTA GCC | AGG | ACA GTA GAA GGA-3' | | 72 | 21 | | |

Thirty-five cycles were performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products were purified using Qia-quick® PCR purification kits (Qiagen cat# 28104; Chatsworth, Calif.). Yield and purity of the PCR product determined spectrophotometrically at $OD_{260}$ on a Beckman DU 650 spectrophotometer.

6.3.2. DNA Sequence Analysis

Fluorescent dye was attached to PCR products for automated sequencing using the Taq Dye Terminator® Kit (Perkin-Elmer cat# 401628). Dideoxy DNA sequencing was performed in both forward and reverse directions on an Applied Biosystems, Inc. (ABI) Foster City, Calif., automated Model 377® sequencer. The software used for analysis of the resulting data was "Sequence Navigator® software" obtained through ABI.

7. EXAMPLE 2

IDENTIFICATION OF THE C3508G MUTATION IN THE BRCA1 GENE

A test BRCA1 gene sample was analyzed for mutations first using ASO analysis, as described in Section 6.1, above.

The test gene was determined to be negative for all eight of the ASO mutations. Exon 11 of the test gene was then analyzed according to the protein truncation assay as described in Section 6.2, above.

Protein products of fragments 1 and 2 of the test sample were normal length of 70 kD and 74 kD, respectively. Fragment 3 of the test sample yielded a 15 kD protein in addition to the normal length 43 kD protein. The occurrence of a nonsense mutation at the point of truncation, which was about one third of the way or about 400 bp (270 bp/10 kD×15 kD=approximately 400 bp) into fragment 3, was tested first, prior to testing for a frameshift mutation at some point upstream of the truncation site. DNA sequence analysis of the coding region around 400 bp from the 5'-end of DNA fragment 3 confirmed the latter possibility that the mutation was a nonsense mutation, designated C3508G, resulting in a premature terminator codon (TCA to TGA) at position 1130 within exon 11 (see FIG. 1).

8. EXAMPLE 3

IDENTIFICATION OF THE 5053DELG MUTATION IN THE BRCA1 GENE

A test BRCA1 gene sample was tested for mutations first using ASO analysis, as described in Section 6.1, above. The test gene was determined to be negative for all eight of the ASO mutations. Exon 11 of the test gene was then analyzed according to the protein truncation assay as described in Section 6.2, above. All three protein fragments were the normal size indicating that exon 11 of the test gene did not contain a protein truncating mutation.

The DNA sequence of the test gene was then analyzed according to the sequencing analysis of Section 6.3, above. Comparison of the patient sequence with the BRCA1$^{(omi)}$ sequence revealed that the patient guanine (G) residue present at nucleotide position 5053 of the BRCA1 gene was deleted in the patient's BRCA1 gene. This deletion causes a frame shift in the coding region of exon 16. The frame shift results in an altered translation of the BRCA1 gene after nucleotide position 5053 until nucleotide positions 5089–5091, where a stop codon (TGA) occurs in the altered reading frame (see FIG. 1).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

---

What is claimed is:

1. A method for determining the presence or absence of a sequence variation in a gene sample, comprising the sequential steps of:
   (a) performing an allele specific hybridization assay for the presence or absence of one or more pre-determined sequence variations;
   (b) if no pre-determined sequence variation is found in step (a), then performing a sequence variation locating assay selected from the group consisting of protein truncation assay, single strand conformation polymorphism analysis, heteroduplex analysis, denaturing gradient gel electrophoresis, constant denaturant gel electrophoresis, and chemical cleavage analysis;
   (c) if no sequence variation is found in step (b), then sequencing the gene sample; and
   (d) determining the presence or absence of a sequence variation by analyzing the sequence(s) obtained in step (c) against a reference sequence.

2. A Method for determining the presence or absence of a sequence variation in a gene sample, comprising the sequential steps of:
   (a) performing an allele specific hybridization assay for the presence of one or more pre-determined sequence variations;
   (b) if no pre-determined sequence variation is found in step (a), then performing a sequence variation locating assay selected from the group consisting of protein truncation assay, single strand conformation polymorphism analysis, heteroduplex analysis, denaturing gradient gel electrophoresis, constant denaturant gel electrophoresis, and chemical cleavage analysis;
   (c) if a sequence variation is detected in step (b), then performing targeted confirmatory sequencing; and
   (d) determining the presence or absence of a sequence variation by analyzing the sequence(s) obtained in step (c) against a reference sequence.

3. A method for determining the presence or absence of a sequence variation in a gene sample, comprising the sequential steps of:
   (a) performing an allele specific hybridization assay for the presence or absence of one or more pre-determined sequence variations; and
   (b) if no pre-determined sequence variation is found in step (a), then sequencing the gene sample; and
   (c) determining the presence or absence of a sequence variation by analyzing the sequence(s) obtained in step (b) against a reference sequence.

4. A method for determining the presence or absence of a sequence variation in a gene sample, comprising the sequential steps of:
   (a) performing a sequence variation locating assay selected from the group consisting of protein truncation assay, single strand conformation polymorphism analysis, heteroduplex analysis, denaturing gradient gel electrophoresis, constant denaturant gel electrophoresis, and chemical cleavage analysis;
   (b) if no sequence variation is found in step (a), then sequencing the gene sample; and
   (c) determining the presence or absence of a sequence variation by analyzing the sequence(s) obtained in step (b) against a reference sequence.

5. The method of claim 1, 2, or 3 further comprising repeating the allele specific hybridization until a predetermined number of known sequence variations have been tested for.

6. The method of claim 5 wherein the allele specific hybridization assay is performed using a dot blot format.

7. The method of claim 5 wherein the allele specific hybridization assay is performed using a multiplex format.

8. The method of claim 1, 2, or 3 wherein the allele specific hybridization comprises testing for a predetermined number of sequence variations in a single step not requiring repetition.

9. The method of claim 8 wherein the allele specific hybridization assay is performed using a reverse dot blot format, a MASDA format, or a chip array format.

10. The method of claim 1, 2, or 4 wherein the sequence variation locating assay is performed using a protein truncation assay.

11. The method of claim 1, 2, or 4 wherein the sequence variation locating assay is performed using a chemical cleavage assay, a heteroduplex analysis, a single strand conformation, polymorphism assay, a constant denaturing gel electrophoresis assay, or a denaturing gradient gel electrophoresis assay.

12. The method of claim 1, 2, 3, or 4 wherein sequencing is performed in only the forward or reverse direction.

13. The method of claim 1, 2, 3, or 4 wherein sequencing is performed in both the forward and reverse directions.

14. The method of claim 1, 2, 3, or 4 wherein sequencing comprises sequencing both exons and introns of the gene or parts thereof.

15. The method of claim 14 wherein all exons and all introns are sequenced from end to end.

16. The method of claim 1, 2, 3, or 4 wherein sequencing comprises sequencing only exons.

17. The method of claim 1, 2, 3, or 4 wherein sequencing comprises sequencing only intronic sequences.

18. The method of claim 1, 2, 3, or 4 wherein the gene sample is a human BRCA1 gene.

19. The method of claim 1, 2, 3, or 4 wherein the reference sequence is a coding sequence.

20. The method of claim 19 wherein the reference sequence is a BRCA1 coding sequence.

21. The method of claim 1, 2, 3, or 4 wherein the reference sequence is a genomic sequence.

22. The method of claim 21 wherein the reference sequence is a BRCA1 genomic sequence.

23. The method of claim 1, 2, 3, or 4 wherein the reference sequence is one or more exons of a gene of interest.

24. The method of claim 1, 2, or 3 wherein the predetermined sequence variation in step (a) is a known mutation.

25. The method of claim 1, 2, 3, or 4, wherein the sequence variation is a known mutation.

* * * * *

SEQUENCE LISTING (1) GENERAL INFORMATION:

(iii) NUMBER OF SEQUENCES: 110

(2) INFORMATION FOR SEQ ID NO:1:

(i) SEQUENCE CHARACTERISTICS:
      (A) LENGTH: 5711 base pairs
      (B) TYPE: nucleic acid
      (C) STRANDEDNESS: Not Relevant
      (D) TOPOLOGY: linear (ii) MOLECULE TYPE: cDNA (vi) ORIGINAL SOURCE:
      (A) ORGANISM: Homo sapiens
      (B) STRAIN: BRCA1

(viii) POSITION IN GENOME:
      (A) CHROMOSOME/SEGMENT: 17
      (B) MAP POSITION: 17q21

(xi) SEQUENCE DESCRIPTION: SEQ ID NO:1:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGT     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540
```

-continued

```
AACCCGAAAA TCCTTCCTTG CAGGAAACCA GTCTCAGTGT CCAACTCTCT AACCTTGGAA    600

CTGTGAGAAC TCTGAGGACA AAGCAGCGGA TACAACCTCA AAAGACGTCT GTCTACATTG    660

AATTGGGATC TGATTCTTCT GAAGATACCG TTAATAAGGC AACTTATTGC AGTGTGGGAG    720

ATCAAGAATT GTTACAAATC ACCCCTCAAG GAACCAGGGA TGAAATCAGT TTGGATTCTG    780

CAAAAAAGGC TGCTTGTGAA TTTTCTGAGA CGGATGTAAC AAATACTGAA CATCATCAAC    840

CCAGTAATAA TGATTTGAAC ACCACTGAGA AGCGTGCAGC TGAGAGGCAT CCAGAAAAGT    900

ATCAGGGTAG TTCTGTTTCA AACTTGCATG TGGAGCCATG TGGCACAAAT ACTCATGCCA    960

GCTCATTACA GCATGAGAAC AGCAGTTTAT TACTCACTAA AGACAGAATG AATGTAGAAA    1020

AGGCTGAATT CTGTAATAAA AGCAAACAGC CTGGCTTAGC AAGGAGCCAA CATAACAGAT    1080

GGGCTGGAAG TAAGGAAACA TGTAATGATA GGCGGACTCC CAGCACAGAA AAAAAGGTAG    1140

ATCTGAATGC TGATCCCCTG TGTGAGAGAA AAGAATGGAA TAAGCAGAAA CTGCCATGCT    1200

CAGAGAATCC TAGAGATACT GAAGATGTTC CTTGGATAAC ACTAAATAGC AGCATTCAGA    1260

AAGTTAATGA GTGGTTTTCC AGAAGTGATG AACTGTTAGG TTCTGATGAC TCACATGATG    1320

GGGAGTCTGA ATCAAATGCC AAAGTAGCTG ATGTATTGGA CGTTCTAAAT GAGGTAGATG    1380

AATATTCTGG TTCTTCAGAG AAAATAGACT TACTGGCCAG TGATCCTCAT GAGGCTTTAA    1440

TATGTAAAAG TGAAAGAGTT CACTCCAAAT CAGTAGAGAG TAATATTGAA GACAAAATAT    1500

TTGGGAAAAC CTATCGGAAG AAGGCAAGCC TCCCCAACTT AAGCCATGTA ACTGAAAATC    1560

TAATTATAGG AGCATTTGTT ACTGAGCCAC AGATAATACA AGAGCGTCCC CTCACAAATA    1620

AATTAAAGCG TAAAAGGAGA CCTACATCAG GCCTTCATCC TGAGGATTTT ATCAAGAAAG    1680

CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCAGAA TGAGAAAAAT CCTAACCCAA TAGAATCACT CGAAAAGAA TCTGCTTTCA    1860

AAACGAAAGC TGAACCTATA AGCAGCAGTA TAAGCAATAT GGAACTCGAA TTAAATATCC    1920

ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG TGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AAGAAGAGAA ACTAGAAACA GTTAAAGTGT    2340

CTAATAATGC TGAAGACCCC AAAGATCTCA TGTTAAGTGG AGAAAGGGTT TTGCAAACTG    2400

AAAGATCTGT AGAGAGTAGC AGTATTTCAC TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880
```

```
AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GGAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GAAGTAGTC     3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAGAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCCTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AAGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG GCAACATACC ATCTTCAACC TCTGCATTGA    4920

AAGTTCCCCA ATTGAAAGTT GCAGAATCTG CCCAGGGTCC AGCTGCTGCT CATACTACTG    4980

ATACTGCTGG GTATAATGCA ATGGAAGAAA GTGTGAGCAG GGAGAAGCCA GAATTGACAG    5040

CTTCAACAGA AAGGGTCAAC AAAAGAATGT CCATGGTGGT GTCTGGCCTG ACCCCAGAAG    5100

AATTTATGCT CGTGTACAAG TTTGCCAGAA AACACCACAT CACTTTAACT AATCTAATTA    5160

CTGAAGAGAC TACTCATGTT GTTATGAAAA CAGATGCTGA GTTTGTGTGT GAACGGACAC    5220

TGAAATATTT TCTAGGAATT GCGGGAGGAA AATGGGTAGT TAGCTATTTC TGGGTGACCC    5280
```

```
AGTCTATTAA AGAAAGAAAA ATGCTGAATG AGCATGATTT TGAAGTCAGA GGAGATGTGG      5340

TCAATGGAAG AAACCACCAA GGTCCAAAGC GAGCAAGAGA ATCCCAGGAC AGAAAGATCT      5400

TCAGGGGGCT AGAAATCTGT TGCTATGGGC CCTTCACCAA CATGCCCACA GATCAACTGG      5460

AATGGATGGT ACAGCTGTGT GGTGCTTCTG TGGTGAAGGA GCTTTCATCA TTCACCCTTG      5520

GCACAGGTGT CCACCCAATT GTGGTTGTGC AGCCAGATGC CTGGACAGAG GACAATGGCT      5580

TCCATGCAAT TGGGCAGATG TGTGAGGCAC CTGTGGTGAC CCGAGAGTGG GTGTTGGACA      5640

GTGTAGCACT CTACCAGTGC CAGGAGCTGG ACACCTACCT GATACCCCAG ATCCCCCACA      5700

GCCACTACTG A                                                          5711
```

(2) INFORMATION FOR SEQ ID NO:2:

(i) SEQUENCE CHARACTERISTICS:
        (A) LENGTH: 1863 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO:2:

```
Met Asp Leu Ser Ala Leu Arg Val Glu Glu Val Gln Asn Val Ile Asn
 1               5                  10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220
```

-continued

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
            325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
            405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
            485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
            565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

-continued

```
Ile Asp Ser Cys Ser Ser Glu Glu Ile Lys Lys Lys Tyr Asn
            645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
            690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                    725                 730                 735

Thr Val Lys Val Ser Asn Asn Ala Glu Asp Pro Lys Asp Leu Met Leu
                    740                 745                 750

Ser Gly Glu Arg Val Leu Gln Thr Glu Arg Ser Val Glu Ser Ser Ser
                    755                 760                 765

Ile Ser Leu Val Pro Gly Thr Asp Tyr Gly Thr Gln Glu Ser Ile Ser
                    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                    820                 825                 830

Leu Gly His Glu Val Asn His Ser Arg Glu Thr Ser Ile Glu Met Glu
                    835                 840                 845

Glu Ser Glu Leu Asp Ala Gln Tyr Leu Gln Asn Thr Phe Lys Val Ser
            850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
                    900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
            930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975

Pro Tyr Arg Ile Pro Pro Leu Phe Pro Ile Lys Ser Phe Val Lys Thr
                    980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Gly Ala Ser
1025                1030                1035                1040

Ser Ser Asn Ile Asn Glu Val Gly Ser Ser Thr Asn Glu Val Gly Ser
            1045                1050                1055

Ser Ile Asn Glu Ile Gly Ser Ser Asp Glu Asn Ile Gln Ala Glu Leu
```

-continued

```
                1060                1065                1070
Gly Arg Asn Arg Gly Pro Lys Leu Asn Ala Met Leu Arg Leu Gly Val
        1075                1080                1085
Leu Gln Pro Glu Val Tyr Lys Gln Ser Leu Pro Gly Ser Asn Cys Lys
    1090                1095                1100
His Pro Glu Ile Lys Lys Gln Glu Tyr Glu Val Val Gln Thr Val
1105                1110                1115                1120
Asn Thr Asp Phe Ser Pro Tyr Leu Ile Ser Asp Asn Leu Glu Gln Pro
            1125                1130                1135
Met Gly Ser Ser His Ala Ser Gln Val Cys Ser Glu Thr Pro Asp Asp
        1140                1145                1150
Leu Leu Asp Asp Gly Glu Ile Lys Glu Asp Thr Ser Phe Ala Glu Asn
        1155                1160                1165
Asp Ile Lys Glu Ser Ser Ala Val Phe Ser Lys Ser Val Gln Arg Gly
    1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
            1205                1210                1215
Ser Ser Glu Asp Glu Glu Leu Pro Cys Phe Gln His Leu Leu Phe Gly
        1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
    1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
            1285                1290                1295
Ser Ser Gln Cys Ser Glu Leu Glu Asp Leu Thr Ala Asn Thr Asn Thr
        1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
    1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
            1365                1370                1375
Ser Val Ser Glu Asp Cys Ser Gly Leu Ser Ser Gln Ser Asp Ile Leu
        1380                1385                1390
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
    1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
            1445                1450                1455
Ser Gln Lys Ser Ser Glu Tyr Pro Ile Ser Gln Asn Pro Glu Gly Leu
        1460                1465                1470
Ser Ala Asp Lys Phe Glu Val Ser Ala Asp Ser Ser Thr Ser Lys Asn
        1475                1480                1485
```

```
Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
                1525                1530                1535

Gln Gln Leu Glu Glu Ser Gly Pro His Asp Leu Thr Glu Thr Ser Tyr
            1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Gly Pro Ala Ala
                1605                1610                1615

Ala His Thr Thr Asp Thr Ala Gly Tyr Asn Ala Met Glu Glu Ser Val
            1620                1625                1630 er Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
                1685                1690                1695

Cys Glu Arg Thr Leu Lys Tyr Phe Leu Gly Ile Ala Gly Gly Lys Trp
            1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
                1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
        1795                1800                1805

Val Val Gln Pro Asp Ala Trp Thr Glu Asp Asn Gly Phe His Ala Ile
    1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
                1845                1850                1855

Gln Ile Pro His Ser His Tyr
            1860

(2) INFORMATION FOR SEQ ID NO:3:

(i) SEQUENCE CHARACTERISTICS:
        (A) LENGTH: 5711 base pairs
        (B) TYPE: nucleic acid
```

(C) STRANDEDNESS: Not Relevant
        (D) TOPOLOGY: linear (ii) MOLECULE TYPE: cDNA (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO:3:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGT     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540

AACCCGAAAA TCCTTCCTTG CAGGAAACCA GTCTCAGTGT CCAACTCTCT AACCTTGGAA     600

CTGTGAGAAC TCTGAGGACA AGCAGCGGA TACAACCTCA AAAGACGTCT GTCTACATTG      660

AATTGGGATC TGATTCTTCT GAAGATACCG TTAATAAGGC AACTTATTGC AGTGTGGGAG     720

ATCAAGAATT GTTACAAATC ACCCCTCAAG GAACCAGGGA TGAAATCAGT TTGGATTCTG     780

CAAAAAAGGC TGCTTGTGAA TTTTCTGAGA CGGATGTAAC AAATACTGAA CATCATCAAC     840

CCAGTAATAA TGATTTGAAC ACCACTGAGA AGCGTGCAGC TGAGAGGCAT CCAGAAAAGT     900

ATCAGGGTAG TTCTGTTTCA AACTTGCATG TGGAGCCATG TGGCACAAAT ACTCATGCCA     960

GCTCATTACA GCATGAGAAC AGCAGTTTAT TACTCACTAA AGACAGAATG AATGTAGAAA    1020

AGGCTGAATT CTGTAATAAA AGCAAACAGC CTGGCTTAGC AAGGAGCCAA CATAACAGAT    1080

GGGCTGGAAG TAAGGAAACA TGTAATGATA GGCGGACTCC CAGCACAGAA AAAAAGGTAG    1140

ATCTGAATGC TGATCCCCTG TGTGAGAGAA AGAATGGAA TAAGCAGAAA CTGCCATGCT     1200

CAGAGAATCC TAGAGATACT GAAGATGTTC CTTGGATAAC ACTAAATAGC AGCATTCAGA    1260

AAGTTAATGA GTGGTTTTCC AGAAGTGATG AACTGTTAGG TTCTGATGAC TCACATGATG    1320

GGGAGTCTGA ATCAAATGCC AAAGTAGCTG ATGTATTGGA CGTTCTAAAT GAGGTAGATG    1380

AATATTCTGG TTCTTCAGAG AAAATAGACT TACTGGCCAG TGATCCTCAT GAGGCTTTAA    1440

TATGTAAAAG TGAAAGAGTT CACTCCAAAT CAGTAGAGAG TAATATTGAA GACAAAATAT    1500

TTGGGAAAAC CTATCGGAAG AAGGCAAGCC TCCCCAACTT AAGCCATGTA ACTGAAAATC    1560

TAATTATAGG AGCATTTGTT ACTGAGCCAC AGATAATACA AGAGCGTCCC CTCACAAATA    1620

AATTAAAGCG TAAAAGGAGA CCTACATCAG GCCTTCATCC TGAGGATTTT ATCAAGAAAG    1680

CAGATTTGGC AGTTCAAAAG ACTCCTGAAA TGATAAATCA GGGAACTAAC CAAACGGAGC    1740

AGAATGGTCA AGTGATGAAT ATTACTAATA GTGGTCATGA GAATAAAACA AAAGGTGATT    1800

CTATTCAGAA TGAAAAAAAT CCTAACCCAA TAGAATCACT CGAAAAGAA TCTGCTTTCA     1860

AAACGAAAGC TGAACCTATA AGCAGCAGTA TAAGCAATAT GGAACTCGAA TTAAATATCC    1920
```

-continued

```
ACAATTCAAA AGCACCTAAA AAGAATAGGC TGAGGAGGAA GTCTTCTACC AGGCATATTC    1980

ATGCGCTTGA ACTAGTAGTC AGTAGAAATC TAAGCCCACC TAATTGTACT GAATTGCAAA    2040

TTGATAGTTG TTCTAGCAGT GAAGAGATAA AGAAAAAAAA GTACAACCAA ATGCCAGTCA    2100

GGCACAGCAG AAACCTACAA CTCATGGAAG GTAAAGAACC TGCAACTGGA GCCAAGAAGA    2160

GTAACAAGCC AAATGAACAG ACAAGTAAAA GACATGACAG CGATACTTTC CCAGAGCTGA    2220

AGTTAACAAA TGCACCTGGT TCTTTTACTA AGTGTTCAAA TACCAGTGAA CTTAAAGAAT    2280

TTGTCAATCC TAGCCTTCCA AGAGAAGAAA AGAAGAGAA ACTAGAAACA GTTAAAGTGT     2340

CTAATAATGC TGAAGACCCC AAAGATCTCA TGTTAAGTGG AGAAAGGGTT TTGCAAACTG    2400

AAAGATCTGT AGAGAGTAGC AGTATTTCAT TGGTACCTGG TACTGATTAT GGCACTCAGG    2460

AAAGTATCTC GTTACTGGAA GTTAGCACTC TAGGGAAGGC AAAAACAGAA CCAAATAAAT    2520

GTGTGAGTCA GTGTGCAGCA TTTGAAAACC CCAAGGGACT AATTCATGGT TGTTCCAAAG    2580

ATAATAGAAA TGACACAGAA GGCTTTAAGT ATCCATTGGG ACATGAAGTT AACCACAGTC    2640

GGGAAACAAG CATAGAAATG GAAGAAAGTG AACTTGATGC TCAGTATTTG CAGAATACAT    2700

TCAAGGTTTC AAAGCGCCAG TCATTTGCTC TGTTTTCAAA TCCAGGAAAT GCAGAAGAGG    2760

AATGTGCAAC ATTCTCTGCC CACTCTGGGT CCTTAAAGAA ACAAAGTCCA AAAGTCACTT    2820

TTGAATGTGA ACAAAAGGAA GAAAATCAAG GAAAGAATGA GTCTAATATC AAGCCTGTAC    2880

AGACAGTTAA TATCACTGCA GGCTTTCCTG TGGTTGGTCA GAAAGATAAG CCAGTTGATA    2940

ATGCCAAATG TAGTATCAAA GGAGGCTCTA GGTTTTGTCT ATCATCTCAG TTCAGAGGCA    3000

ACGAAACTGG ACTCATTACT CCAAATAAAC ATGGACTTTT ACAAAACCCA TATCGTATAC    3060

CACCACTTTT TCCCATCAAG TCATTTGTTA AAACTAAATG TAAGAAAAAT CTGCTAGAGG    3120

AAAACTTTGA GGAACATTCA ATGTCACCTG AAAGAGAAAT GGGAAATGAG AACATTCCAA    3180

GTACAGTGAG CACAATTAGC CGTAATAACA TTAGAGAAAA TGTTTTTAAA GAAGCCAGCT    3240

CAAGCAATAT TAATGAAGTA GGTTCCAGTA CTAATGAAGT GGGCTCCAGT ATTAATGAAA    3300

TAGGTTCCAG TGATGAAAAC ATTCAAGCAG AACTAGGTAG AAACAGAGGG CCAAAATTGA    3360

ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAAAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320
```

```
AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCTTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AAGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG GCAACATACC ATCTTCAACC TCTGCATTGA    4920

AAGTTCCCCA ATTGAAAGTT GCAGAATCTG CCCAGAGTCC AGCTGCTGCT CATACTACTG    4980

ATACTGCTGG GTATAATGCA ATGGAAGAAA GTGTGAGCAG GGAGAAGCCA GAATTGACAG    5040

CTTCAACAGA AAGGGTCAAC AAAAGAATGT CCATGGTGGT GTCTGGCCTG ACCCCAGAAG    5100

AATTTATGCT CGTGTACAAG TTTGCCAGAA AACACCACAT CACTTTAACT AATCTAATTA    5160

CTGAAGAGAC TACTCATGTT GTTATGAAAA CAGATGCTGA GTTTGTGTGT GAACGGACAC    5220

TGAAATATTT TCTAGGAATT GCGGGAGGAA AATGGGTAGT TAGCTATTTC TGGGTGACCC    5280

AGTCTATTAA AGAAAGAAAA ATGCTGAATG AGCATGATTT TGAAGTCAGA GGAGATGTGG    5340

TCAATGGAAG AAACCACCAA GGTCCAAAGC GAGCAAGAGA ATCCCAGGAC AGAAAGATCT    5400

TCAGGGGGCT AGAAATCTGT TGCTATGGGC CCTTCACCAA CATGCCCACA GATCAACTGG    5460

AATGGATGGT ACAGCTGTGT GGTGCTTCTG TGGTGAAGGA GCTTTCATCA TTCACCCTTG    5520

GCACAGGTGT CCACCCAATT GTGGTTGTGC AGCCAGATGC CTGGACAGAG GACAATGGCT    5580

TCCATGCAAT TGGGCAGATG TGTGAGGCAC CTGTGGTGAC CCGAGAGTGG GTGTTGGACA    5640

GTGTAGCACT CTACCAGTGC CAGGAGCTGG ACACCTACCT GATACCCCAG ATCCCCCACA    5700

GCCACTACTG A                                                        5711
```

(2) INFORMATION FOR SEQ ID NO:4:

(i) SEQUENCE CHARACTERISTICS:
        (A) LENGTH: 1863 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO:4:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45
```

-continued

```
Leu Lys Leu Leu Asn Gln Lys Lys Gly Pro Ser Gln Cys Pro Leu Cys
 50                  55                  60

Lys Asn Asp Ile Thr Lys Arg Ser Leu Gln Glu Ser Thr Arg Phe Ser
 65                  70                  75                  80

Gln Leu Val Glu Glu Leu Leu Lys Ile Ile Cys Ala Phe Gln Leu Asp
                     85                  90                  95

Thr Gly Leu Glu Tyr Ala Asn Ser Tyr Asn Phe Ala Lys Lys Glu Asn
                    100                 105                 110

Asn Ser Pro Glu His Leu Lys Asp Glu Val Ser Ile Ile Gln Ser Met
                115                 120                 125

Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                    165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
                195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
                275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
                355                 360                 365

Asp Val Pro Trp Ile Thr Leu Asn Ser Ser Ile Gln Lys Val Asn Glu
                370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
```

-continued

```
465                 470                 475                 480
Leu Ile Ile Gly Ala Phe Val Thr Glu Pro Gln Ile Gln Glu Arg
                485                 490                 495

Pro Leu Thr Asn Lys Leu Lys Arg Lys Arg Pro Thr Ser Gly Leu
                500                 505                 510

His Pro Glu Asp Phe Ile Lys Lys Ala Asp Leu Ala Val Gln Lys Thr
                515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
                595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
    850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895
```

```
Pro Lys Val Thr Phe Glu Cys Glu Gln Lys Glu Asn Gln Gly Lys
            900                 905                 910
Asn Glu Ser Asn Ile Lys Pro Val Gln Thr Val Asn Ile Thr Ala Gly
            915                 920                 925
Phe Pro Val Val Gly Gln Lys Asp Lys Pro Val Asp Asn Ala Lys Cys
            930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
            965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
            995                 1000                1005
Ser Pro Glu Arg Glu Met Gly Asn Glu Asn Ile Pro Ser Thr Val Ser
            1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
            1045                1050                1055
Ser Ile Asn Glu Ile Gly Ser Ser Asp Glu Asn Ile Gln Ala Glu Leu
            1060                1065                1070
Gly Arg Asn Arg Gly Pro Lys Leu Asn Ala Met Leu Arg Leu Gly Val
            1075                1080                1085
Leu Gln Pro Glu Val Tyr Lys Gln Ser Leu Pro Gly Ser Asn Cys Lys
            1090                1095                1100
His Pro Glu Ile Lys Lys Gln Glu Tyr Glu Glu Val Val Gln Thr Val
1105                1110                1115                1120
Asn Thr Asp Phe Ser Pro Tyr Leu Ile Ser Asp Asn Leu Glu Gln Pro
            1125                1130                1135
Met Gly Ser Ser His Ala Ser Gln Val Cys Ser Glu Thr Pro Asp Asp
            1140                1145                1150
Leu Leu Asp Asp Gly Glu Ile Lys Glu Asp Thr Ser Phe Ala Glu Asn
            1155                1160                1165
Asp Ile Lys Glu Ser Ser Ala Val Phe Ser Lys Ser Val Gln Lys Gly
            1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
            1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
            1235                1240                1245
Thr Glu Cys Leu Ser Lys Asn Thr Glu Glu Asn Leu Leu Ser Leu Lys
            1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
            1285                1290                1295
Ser Ser Gln Cys Ser Glu Leu Glu Asp Leu Thr Ala Asn Thr Asn Thr
            1300                1305                1310
```

-continued

```
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
        1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
        1365                1370                1375
Ser Val Ser Glu Asp Cys Ser Gly Leu Ser Ser Gln Ser Asp Ile Leu
        1380                1385                1390
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
        1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Ala Val Leu Thr
        1445                1450                1455
Ser Gln Lys Ser Ser Glu Tyr Pro Ile Ser Gln Asn Pro Glu Gly Leu
        1460                1465                1470
Ser Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser Leu
        1490                1495                1500
Asp Asp Arg Trp Tyr Met His Ser Cys Ser Gly Ser Leu Gln Asn Arg
1505                1510                1515                1520
Asn Tyr Pro Ser Gln Glu Glu Leu Ile Lys Val Val Asp Val Glu Glu
        1525                1530                1535
Gln Gln Leu Glu Glu Ser Gly Pro His Asp Leu Thr Glu Thr Ser Tyr
        1540                1545                1550
Leu Pro Arg Gln Asp Leu Glu Gly Thr Pro Tyr Leu Glu Ser Gly Ile
        1555                1560                1565
Ser Leu Phe Ser Asp Asp Pro Glu Ser Asp Pro Ser Glu Asp Arg Ala
        1570                1575                1580
Pro Glu Ser Ala Arg Val Gly Asn Ile Pro Ser Ser Thr Ser Ala Leu
1585                1590                1595                1600
Lys Val Pro Gln Leu Lys Val Ala Glu Ser Ala Gln Ser Pro Ala Ala
        1605                1610                1615
Ala His Thr Thr Asp Thr Ala Gly Tyr Asn Ala Met Glu Glu Ser Val
        1620                1625                1630
Ser Arg Glu Lys Pro Glu Leu Thr Ala Ser Thr Glu Arg Val Asn Lys
        1635                1640                1645
Arg Met Ser Met Val Val Ser Gly Leu Thr Pro Glu Glu Phe Met Leu
        1650                1655                1660
Val Tyr Lys Phe Ala Arg Lys His His Ile Thr Leu Thr Asn Leu Ile
1665                1670                1675                1680
Thr Glu Glu Thr Thr His Val Val Met Lys Thr Asp Ala Glu Phe Val
        1685                1690                1695
Cys Glu Arg Thr Leu Lys Tyr Phe Leu Gly Ile Ala Gly Gly Lys Trp
        1700                1705                1710
Val Val Ser Tyr Phe Trp Val Thr Gln Ser Ile Lys Glu Arg Lys Met
        1715                1720                1725
Leu Asn Glu His Asp Phe Glu Val Arg Gly Asp Val Val Asn Gly Arg
```

```
                    1730              1735              1740
Asn His Gln Gly Pro Lys Arg Ala Arg Glu Ser Gln Asp Arg Lys Ile
1745              1750              1755              1760

Phe Arg Gly Leu Glu Ile Cys Cys Tyr Gly Pro Phe Thr Asn Met Pro
            1765              1770              1775

Thr Asp Gln Leu Glu Trp Met Val Gln Leu Cys Gly Ala Ser Val Val
        1780              1785              1790

Lys Glu Leu Ser Ser Phe Thr Leu Gly Thr Gly Val His Pro Ile Val
        1795              1800              1805

Val Val Gln Pro Asp Ala Trp Thr Glu Asp Asn Gly Phe His Ala Ile
    1810              1815              1820

Gly Gln Met Cys Glu Ala Pro Val Val Thr Arg Glu Trp Val Leu Asp
1825              1830              1835              1840

Ser Val Ala Leu Tyr Gln Cys Gln Glu Leu Asp Thr Tyr Leu Ile Pro
            1845              1850              1855

Gln Ile Pro His Ser His Tyr
        1860
```

(2) INFORMATION FOR SEQ ID NO:5:

(i) SEQUENCE CHARACTERISTICS:
        (A) LENGTH: 5711 base pairs
        (B) TYPE: nucleic acid
        (C) STRANDEDNESS: Not Relevant
        (D) TOPOLOGY: linear (ii) MOLECULE TYPE: cDNA (vi) ORIGINAL SOURCE:
        (A) ORGANISM: Homo sapiens
        (B) STRAIN: BRCA1

(viii) POSITION IN GENOME:
        (A) CHROMOSOME/SEGMENT: 17
        (B) MAP POSITION: 17q21

(xi) SEQUENCE DESCRIPTION: SEQ ID NO:5:

```
AGCTCGCTGA GACTTCCTGG ACCCCGCACC AGGCTGTGGG GTTTCTCAGA TAACTGGGCC      60

CCTGCGCTCA GGAGGCCTTC ACCCTCTGCT CTGGGTAAAG TTCATTGGAA CAGAAAGAAA     120

TGGATTTATC TGCTCTTCGC GTTGAAGAAG TACAAAATGT CATTAATGCT ATGCAGAAAA     180

TCTTAGAGTG TCCCATCTGT CTGGAGTTGA TCAAGGAACC TGTCTCCACA AAGTGTGACC     240

ACATATTTTG CAAATTTTGC ATGCTGAAAC TTCTCAACCA GAAGAAAGGG CCTTCACAGT     300

GTCCTTTATG TAAGAATGAT ATAACCAAAA GGAGCCTACA AGAAAGTACG AGATTTAGTC     360

AACTTGTTGA AGAGCTATTG AAAATCATTT GTGCTTTTCA GCTTGACACA GGTTTGGAGT     420

ATGCAAACAG CTATAATTTT GCAAAAAAGG AAAATAACTC TCCTGAACAT CTAAAAGATG     480

AAGTTTCTAT CATCCAAAGT ATGGGCTACA GAAACCGTGC CAAAAGACTT CTACAGAGTG     540

AACCCGAAAA TCCTTCCTTG CAGGAAACCA GTCTCAGTGT CCAACTCTCT AACCTTGGAA     600

CTGTGAGAAC TCTGAGGACA AAGCAGCGGA TACAACCTCA AAAGACGTCT GTCTACATTG     660

AATTGGGATC TGATTCTTCT GAAGATACCG TTAATAAGGC AACTTATTGC AGTGTGGGAG     720

ATCAAGAATT GTTACAAATC ACCCCTCAAG GAACCAGGGA TGAAATCAGT TTGGATTCTG     780

CAAAAAAGGC TGCTTGTGAA TTTTCTGAGA CGGATGTAAC AAATACTGAA CATCATCAAC     840

CCAGTAATAA TGATTTGAAC ACCACTGAGA AGCGTGCAGC TGAGAGGCAT CCAGAAAAGT     900

ATCAGGGTAG TTCTGTTTCA AACTTGCATG TGGAGCCATG TGGCACAAAT ACTCATGCCA     960
```

-continued

```
GCTCATTACA GCATGAGAAC AGCAGTTTAT TACTCACTAA AGACAGAATG AATGTAGAAA      1020

AGGCTGAATT CTGTAATAAA AGCAAACAGC CTGGCTTAGC AAGGAGCCAA CATAACAGAT      1080

GGGCTGGAAG TAAGGAAACA TGTAATGATA GGCGGACTCC CAGCACAGAA AAAAAGGTAG      1140

ATCTGAATGC TGATCCCCTG TGTGAGAGAA AGAATGGAA TAAGCAGAAA CTGCCATGCT       1200

CAGAGAATCC TAGAGATACT GAAGATGTTC CTTGGATAAC ACTAAATAGC AGCATTCAGA      1260

AAGTTAATGA GTGGTTTTCC AGAAGTGATG AACTGTTAGG TTCTGATGAC TCACATGATG      1320

GGGAGTCTGA ATCAAATGCC AAAGTAGCTG ATGTATTGGA CGTTCTAAAT GAGGTAGATG      1380

AATATTCTGG TTCTTCAGAG AAAATAGACT TACTGGCCAG TGATCCTCAT GAGGCTTTAA      1440

TATGTAAAAG TGAAAGAGTT CACTCCAAAT CAGTAGAGAG TAATATTGAA GACAAAATAT      1500

TTGGGAAAAC CTATCGGAAG AAGGCAAGCC TCCCCAACTT AAGCCATGTA ACTGAAAATC      1560

TAATTATAGG AGCATTTGTT ACTGAGCCAC AGATAATACA AGAGCGTCCC CTCACAAATA      1620

AATTAAAGCG TAAAAGGAGA CCTACATCAG GCCTTCATCC TGAGGATTTT ATCAAGAAAG      1680

CAGATTTGGC AGTTCAAAAG ACTCCTGAAA TGATAAATCA GGGAACTAAC CAAACGGAGC      1740

AGAATGGTCA AGTGATGAAT ATTACTAATA GTGGTCATGA GAATAAAACA AAAGGTGATT      1800

CTATTCAGAA TGAGAAAAAT CCTAACCCAA TAGAATCACT CGAAAAGAA TCTGCTTTCA       1860

AAACGAAAGC TGAACCTATA AGCAGCAGTA TAAGCAATAT GGAACTCGAA TTAAATATCC      1920

ACAATTCAAA AGCACCTAAA AAGAATAGGC TGAGGAGGAA GTCTTCTACC AGGCATATTC      1980

ATGCGCTTGA ACTAGTAGTC AGTAGAAATC TAAGCCCACC TAATTGTACT GAATTGCAAA      2040

TTGATAGTTG TTCTAGCAGT GAAGAGATAA AGAAAAAAAA GTACAACCAA ATGCCAGTCA      2100

GGCACAGCAG AAACCTACAA CTCATGGAAG GTAAAGAACC TGCAACTGGA GCCAAGAAGA      2160

GTAACAAGCC AAATGAACAG ACAAGTAAAA GACATGACAG TGATACTTTC CCAGAGCTGA      2220

AGTTAACAAA TGCACCTGGT TCTTTTACTA AGTGTTCAAA TACCAGTGAA CTTAAAGAAT      2280

TTGTCAATCC TAGCCTTCCA AGAGAAGAAA AAGAAGAGAA ACTAGAAACA GTTAAAGTGT      2340

CTAATAATGC TGAAGACCCC AAAGATCTCA TGTTAAGTGG AGAAAGGGTT TTGCAAACTG      2400

AAAGATCTGT AGAGAGTAGC AGTATTTCAC TGGTACCTGG TACTGATTAT GGCACTCAGG      2460

AAAGTATCTC GTTACTGGAA GTTAGCACTC TAGGGAAGGC AAAAACAGAA CCAAATAAAT      2520

GTGTGAGTCA GTGTGCAGCA TTTGAAAACC CCAAGGGACT AATTCATGGT TGTTCCAAAG      2580

ATAATAGAAA TGCACAGAA GGCTTTAAGT ATCCATTGGG ACATGAAGTT AACCACAGTC       2640

GGGAAACAAG CATAGAAATG GAAGAAAGTG AACTTGATGC TCAGTATTTG CAGAATACAT      2700

TCAAGGTTTC AAAGCGCCAG TCATTTGCTC TGTTTTCAAA TCCAGGAAAT GCAGAAGAGG      2760

AATGTGCAAC ATTCTCTGCC CACTCTGGGT CCTTAAAGAA ACAAAGTCCA AAAGTCACTT      2820

TTGAATGTGA ACAAAAGGAA GAAAATCAAG GAAAGAATGA GTCTAATATC AAGCCTGTAC      2880

AGACAGTTAA TATCACTGCA GGCTTTCCTG TGGTTGGTCA GAAAGATAAG CCAGTTGATA      2940

ATGCCAAATG TAGTATCAAA GGAGGCTCTA GGTTTTGTCT ATCATCTCAG TTCAGAGGCA      3000

ACGAAACTGG ACTCATTACT CCAAATAAAC ATGGACTTTT ACAAAACCCA TATCGTATAC      3060

CACCACTTTT TCCCATCAAG TCATTTGTTA AAACTAAATG TAAGAAAAAT CTGCTAGAGG      3120

AAAACTTTGA GGAACATTCA ATGTCACCTG AAAGAGAAAT GGGAAATGAG AACATTCCAA      3180

GTACAGTGAG CACAATTAGC CGTAATAACA TTAGAGAAAA TGTTTTTAAA GGAGCCAGCT      3240

CAAGCAATAT TAATGAAGTA GGTTCCAGTA CTAATGAAGT GGGCTCCAGT ATTAATGAAA      3300

TAGGTTCCAG TGATGAAAAC ATTCAAGCAG AACTAGGTAG AAACAGAGGG CCAAAATTGA      3360
```

```
ATGCTATGCT TAGATTAGGG GTTTTGCAAC CTGAGGTCTA TAAACAAAGT CTTCCTGGAA    3420

GTAATTGTAA GCATCCTGAA ATAAAAAAGC AAGAATATGA AGAAGTAGTT CAGACTGTTA    3480

ATACAGATTT CTCTCCATAT CTGATTTCAG ATAACTTAGA ACAGCCTATG GGAAGTAGTC    3540

ATGCATCTCA GGTTTGTTCT GAGACACCTG ATGACCTGTT AGATGATGGT GAAATAAAGG    3600

AAGATACTAG TTTTGCTGAA AATGACATTA AGGAAAGTTC TGCTGTTTTT AGCAAAAGCG    3660

TCCAGAGAGG AGAGCTTAGC AGGAGTCCTA GCCCTTTCAC CCATACACAT TTGGCTCAGG    3720

GTTACCGAAG AGGGGCCAAG AAATTAGAGT CCTCAGAAGA GAACTTATCT AGTGAGGATG    3780

AAGAGCTTCC CTGCTTCCAA CACTTGTTAT TTGGTAAAGT AAACAATATA CCTTCTCAGT    3840

CTACTAGGCA TAGCACCGTT GCTACCGAGT GTCTGTCTAA GAACACAGAG GAGAATTTAT    3900

TATCATTGAA GAATAGCTTA AATGACTGCA GTAACCAGGT AATATTGGCA AAGGCATCTC    3960

AGGAACATCA CCTTAGTGAG GAAACAAAAT GTTCTGCTAG CTTGTTTTCT TCACAGTGCA    4020

GTGAATTGGA AGACTTGACT GCAAATACAA ACACCCAGGA TCCTTTCTTG ATTGGTTCTT    4080

CCAAACAAAT GAGGCATCAG TCTGAAAGCC AGGGAGTTGG TCTGAGTGAC AAGGAATTGG    4140

TTTCAGATGA TGAAGAAAGA GGAACGGGCT TGGAAGAAAA TAATCAAGAA GAGCAAAGCA    4200

TGGATTCAAA CTTAGGTGAA GCAGCATCTG GGTGTGAGAG TGAAACAAGC GTCTCTGAAG    4260

ACTGCTCAGG GCTATCCTCT CAGAGTGACA TTTTAACCAC TCAGCAGAGG GATACCATGC    4320

AACATAACCT GATAAAGCTC CAGCAGGAAA TGGCTGAACT AGAAGCTGTG TTAGAACAGC    4380

ATGGGAGCCA GCCTTCTAAC AGCTACCCTT CCATCATAAG TGACTCTTCT GCCCTTGAGG    4440

ACCTGCGAAA TCCAGAACAA AGCACATCAG AAAAAGCAGT ATTAACTTCA CAGAAAAGTA    4500

GTGAATACCC TATAAGCCAG AATCCAGAAG GCCTTTCTGC TGACAAGTTT GAGGTGTCTG    4560

CAGATAGTTC TACCAGTAAA AATAAAGAAC CAGGAGTGGA AAGGTCATCC CCTTCTAAAT    4620

GCCCATCATT AGATGATAGG TGGTACATGC ACAGTTGCTC TGGGAGTCTT CAGAATAGAA    4680

ACTACCCATC TCAAGAGGAG CTCATTAAGG TTGTTGATGT GGAGGAGCAA CAGCTGGAAG    4740

AGTCTGGGCC ACACGATTTG ACGGAAACAT CTTACTTGCC AAGGCAAGAT CTAGAGGGAA    4800

CCCCTTACCT GGAATCTGGA ATCAGCCTCT TCTCTGATGA CCCTGAATCT GATCCTTCTG    4860

AAGACAGAGC CCCAGAGTCA GCTCGTGTTG GCAACATACC ATCTTCAACC TCTGCATTGA    4920

AAGTTCCCCA ATTGAAAGTT GCAGAATCTG CCCAGGGTCC AGCTGCTGCT CATACTACTG    4980

ATACTGCTGG GTATAATGCA ATGGAAGAAA GTGTGAGCAG GGAGAAGCCA GAATTGACAG    5040

CTTCAACAGA AAGGGTCAAC AAAAGAATGT CCATGGTGGT GTCTGGCCTG ACCCCAGAAG    5100

AATTTATGCT CGTGTACAAG TTTGCCAGAA ACACCACAT CACTTTAACT AATCTAATTA    5160

CTGAAGAGAC TACTCATGTT GTTATGAAAA CAGATGCTGA GTTTGTGTGT GAACGGACAC    5220

TGAAATATTT TCTAGGAATT GCGGGAGGAA ATGGGTAGT TAGCTATTTC TGGGTGACCC    5280

AGTCTATTAA AGAAAGAAAA ATGCTGAATG AGCATGATTT TGAAGTCAGA GGAGATGTGG    5340

TCAATGGAAG AAACCACCAA GGTCCAAAGC GAGCAAGAGA ATCCCAGGAC AGAAAGATCT    5400

TCAGGGGCT AGAAATCTGT TGCTATGGGC CCTTCACCAA CATGCCCACA GATCAACTGG    5460

AATGGATGGT ACAGCTGTGT GGTGCTTCTG TGGTGAAGGA GCTTTCATCA TTCACCCTTG    5520

GCACAGGTGT CCACCCAATT GTGGTTGTGC AGCCAGATGC CTGGACAGAG GACAATGGCT    5580

TCCATGCAAT TGGGCAGATG TGTGAGGCAC CTGTGGTGAC CCGAGAGTGG GTGTTGGACA    5640

GTGTAGCACT CTACCAGTGC CAGGAGCTGG ACACCTACCT GATACCCCAG ATCCCCCACA    5700
```

```
                                    -continued
GCCACTACTG A                                                                 5711
```

(2) INFORMATION FOR SEQ ID NO:6:

(i) SEQUENCE CHARACTERISTICS:
  (A) LENGTH: 1863 amino acids
  (B) TYPE: amino acid
  (C) STRANDEDNESS: Not Relevant
  (D) TOPOLOGY: Not Relevant (ii) MOLECULE TYPE: protein (vi) ORIGINAL SOURCE:
  (A) ORGANISM: Homo sapiens
  (B) STRAIN: BRCA1

(viii) POSITION IN GENOME:
  (A) CHROMOSOME/SEGMENT: 17
  (B) MAP POSITION: 17q21

(xi) SEQUENCE DESCRIPTION: SEQ ID NO:6:

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
290                 295                 300
```

-continued

```
Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
690                 695                 700

Ala Pro Gly Ser Phe Thr Lys Cys Ser Asn Thr Ser Glu Leu Lys Glu
705                 710                 715                 720
```

-continued

```
Phe Val Asn Pro Ser Leu Pro Arg Glu Glu Lys Glu Lys Leu Glu
            725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
            770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                    820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
                    900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
            930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975

Pro Tyr Arg Ile Pro Pro Leu Phe Pro Ile Lys Ser Phe Val Lys Thr
                    980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val Ser
    1010                1015                1020

Thr Ile Ser Arg Asn Asn Ile Arg Glu Asn Val Phe Lys Gly Ala Ser
1025                1030                1035                1040

Ser Ser Asn Ile Asn Glu Val Gly Ser Ser Thr Asn Glu Val Gly Ser
                1045                1050                1055

Ser Ile Asn Glu Ile Gly Ser Ser Asp Glu Asn Ile Gln Ala Glu Leu
            1060                1065                1070

Gly Arg Asn Arg Gly Pro Lys Leu Asn Ala Met Leu Arg Leu Gly Val
            1075                1080                1085

Leu Gln Pro Glu Val Tyr Lys Gln Ser Leu Pro Gly Ser Asn Cys Lys
    1090                1095                1100

His Pro Glu Ile Lys Lys Gln Glu Tyr Glu Glu Val Val Gln Thr Val
1105                1110                1115                1120

Asn Thr Asp Phe Ser Pro Tyr Leu Ile Ser Asp Asn Leu Glu Gln Pro
                1125                1130                1135

Met Gly Ser Ser His Ala Ser Gln Val Cys Ser Glu Thr Pro Asp Asp
```

-continued

```
                1140                1145                1150
Leu Leu Asp Asp Gly Glu Ile Lys Glu Asp Thr Ser Phe Ala Glu Asn
        1155                1160                1165

Asp Ile Lys Glu Ser Ser Ala Val Phe Ser Lys Ser Val Gln Arg Gly
    1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
            1205                1210                1215

Ser Ser Glu Asp Glu Glu Leu Pro Cys Phe Gln His Leu Leu Phe Gly
        1220                1225                1230

Lys Val Asn Asn Ile Pro Ser Gln Ser Thr Arg His Ser Thr Val Ala
    1235                1240                1245

Thr Glu Cys Leu Ser Lys Asn Thr Glu Glu Asn Leu Leu Ser Leu Lys
1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
            1285                1290                1295

Ser Ser Gln Cys Ser Glu Leu Glu Asp Leu Thr Ala Asn Thr Asn Thr
        1300                1305                1310

Gln Asp Pro Phe Leu Ile Gly Ser Ser Lys Gln Met Arg His Gln Ser
    1315                1320                1325

Glu Ser Gln Gly Val Gly Leu Ser Asp Lys Glu Leu Val Ser Asp Asp
        1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
            1365                1370                1375

Ser Val Ser Glu Asp Cys Ser Gly Leu Ser Ser Gln Ser Asp Ile Leu
        1380                1385                1390

Thr Thr Gln Gln Arg Asp Thr Met Gln His Asn Leu Ile Lys Leu Gln
    1395                1400                1405

Gln Glu Met Ala Glu Leu Glu Ala Val Leu Glu Gln His Gly Ser Gln
    1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Ala Val Leu Thr
            1445                1450                1455

Ser Gln Lys Ser Ser Glu Tyr Pro Ile Ser Gln Asn Pro Glu Gly Leu
        1460                1465                1470

Ser Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Ser Gln Glu Glu Leu Ile Lys Val Val Asp Val Glu Glu
            1525                1530                1535

Gln Gln Leu Glu Glu Ser Gly Pro His Asp Leu Thr Glu Thr Ser Tyr
        1540                1545                1550

Leu Pro Arg Gln Asp Leu Glu Gly Thr Pro Tyr Leu Glu Ser Gly Ile
    1555                1560                1565
```

-continued

```
Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Gly Pro Ala Ala
            1605                1610                1615

Ala His Thr Thr Asp Thr Ala Gly Tyr Asn Ala Met Glu Glu Ser Val
            1620                1625                1630

Ser Arg Glu Lys Pro Glu Leu Thr Ala Ser Thr Glu Arg Val Asn Ly
        1635                1640                1645

Arg Met Ser Met Val Val Ser Gly Leu Thr Pro Glu Glu Phe Met Leu
    1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
            1685                1690                1695

Cys Glu Arg Thr Leu Lys Tyr Phe Leu Gly Ile Ala Gly Lys Trp
            1700                1705                1710

Val Val Ser Tyr Phe Trp Val Thr Gln Ser Ile Lys Glu Arg Lys Met
            1715                1720                1725

Leu Asn Glu His Asp Phe Glu Val Arg Gly Asp Val Val Asn Gly Arg
    1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
            1765                1770                1775

Thr Asp Gln Leu Glu Trp Met Val Gln Leu Cys Gly Ala Ser Val Val
            1780                1785                1790

Lys Glu Leu Ser Ser Phe Thr Leu Gly Thr Gly Val His Pro Ile Val
            1795                1800                1805

Val Val Gln Pro Asp Ala Trp Thr Glu Asp Asn Gly Phe His Ala Ile
    1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
            1845                1850                1855

Gln Ile Pro His Ser His Tyr
            1860
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 2F primer (xi) SEQUENCE DESCRIPTION: SEQ ID NO:7:

GAAGTTGTCA TTTTATAAAC CTTT    24

(2) INFORMATION FOR SEQ ID NO:8:

(i) SEQUENCE CHARACTERISTICS:
           (A) LENGTH: 22 base pairs
           (B) TYPE: nucleic acid
           (C) STRANDEDNESS: Not Relevant
           (D) TOPOLOGY: linear (ii) MOLECULE TYPE: DNA (genomic)

(vi) ORIGINAL SOURCE:
           (B) STRAIN: 2R primer (xi) SEQUENCE DESCRIPTION: SEQ ID NO:8:

TGTCTTTTCT TCCCTAGTAT GT                                          22

(2) INFORMATION FOR SEQ ID NO:9:

(i) SEQUENCE CHARACTERISTICS:
           (A) LENGTH: 21 base pairs
           (B) TYPE: nucleic acid
           (C) STRANDEDNESS: Not Relevant
           (D) TOPOLOGY: linear (ii) MOLECULE TYPE: DNA (genomic)

(vi) ORIGINAL SOURCE:
           (B) STRAIN: 3F primer (xi) SEQUENCE DESCRIPTION: SEQ ID NO:9:

TCCTGACACA GCAGACATTT A                                           21

(2) INFORMATION FOR SEQ ID NO:10:

(i) SEQUENCE CHARACTERISTICS:
           (A) LENGTH: 21 base pairs
           (B) TYPE: nucleic acid
           (C) STRANDEDNESS: Not Relevant
           (D) TOPOLOGY: linear (ii) MOLECULE TYPE: DNA (genomic)

(vi) ORIGINAL SOURCE:
           (B) STRAIN: 3R primer (xi) SEQUENCE DESCRIPTION: SEQ ID NO:10:

TTGGATTTTC GTTCTCACTT A                                           21

(2) INFORMATION FOR SEQ ID NO:11:

(i) SEQUENCE CHARACTERISTICS:
           (A) LENGTH: 20 base pairs
           (B) TYPE: nucleic acid
           (C) STRANDEDNESS: Not Relevant
           (D) TOPOLOGY: linear (ii) MOLECULE TYPE: DNA (genomic)

(vi) ORIGINAL SOURCE:
           (B) STRAIN: 5F primer (xi) SEQUENCE DESCRIPTION: SEQ ID NO:11:

CTCTTAAGGG CAGTTGTGAG                                             20

(2) INFORMATION FOR SEQ ID NO:12:

(i) SEQUENCE CHARACTERISTICS:
           (A) LENGTH: 20 base pairs
           (B) TYPE: nucleic acid
           (C) STRANDEDNESS: Not Relevant
           (D) TOPOLOGY: linear (ii) MOLECULE TYPE: DNA (genomic)

```
    (vi) ORIGINAL SOURCE:
         (B) STRAIN: 5R-M13* primer (xi) SEQUENCE DESCRIPTION: SEQ ID NO:12:

TTCCTACTGT GGTTGCTTCC                                                  20

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 6/7F primer (xi) SEQUENCE DESCRIPTION: SEQ ID NO:13:

CTTATTTTAG TGTCCTTAAA AGG                                              23

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 6R (xi) SEQUENCE DESCRIPTION: SEQ ID NO:14:

TTTCATGGAC AGCACTTGAG TG                                               22

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 7F primer (xi) SEQUENCE DESCRIPTION: SEQ ID NO:15:

CACAACAAAG AGCATACATA GGG                                              23

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 6/7R primer (xi) SEQUENCE DESCRIPTION: SEQ ID NO:16:

TCGGGTTCAC TCTGTAGAAG                                                  20
```

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 8F1 primer (xi) SEQUENCE DESCRIPTION: SEQ ID NO:17:

TTCTCTTCAG GAGGAAAAGC A                                    21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 8R1 primer (xi) SEQUENCE DESCRIPTION: SEQ ID NO:18:

GCTGCCTACC ACAAATACAA A                                    21

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 9F primer (xi) SEQUENCE DESCRIPTION: SEQ ID NO:19:

CCACAGTAGA TGCTCAGTAA ATA                                  23

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 9R primer (xi) SEQUENCE DESCRIPTION: SEQ ID NO:20:

TAGGAAAATA CCAGCTTCAT AGA                                  23

(2) INFORMATION FOR SEQ ID NO:21:

(i) SEQUENCE CHARACTERISTICS:
        (A) LENGTH: 20 base pairs
        (B) TYPE: nucleic acid (C) STRANDEDNESS: Not Relevant
        (D) TOPOLOGY: linear (ii) MOLECULE TYPE: DNA (genomic)

(vi) ORIGINAL SOURCE:
        (B) STRAIN: 10F primer (xi) SEQUENCE DESCRIPTION: SEQ ID NO:21:

TGGTCAGCTT TCTGTAATCG                                           20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 10R primer (xi) SEQUENCE DESCRIPTION: SEQ ID NO:22:

GTATCTACCC ACTCTCTTCT TCAG                                      24

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11AF primer (xi) SEQUENCE DESCRIPTION: SEQ ID NO:23:

CCACCTCCAA GGTGTATCA                                            19

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11AR primer (xi) SEQUENCE DESCRIPTION: SEQ ID NO:24:

TGTTATGTTG GCTCCTTGCT                                           20

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11BF1 primer (xi) SEQUENCE DESCRIPTION: SEQ ID NO:25:

CACTAAAGAC AGAATGAATC TA                                                 22

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11BR1 primer (xi) SEQUENCE DESCRIPTION: SEQ ID NO:26:

GAAGAACCAG AATATTCATC TA                                                 22

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11CF1 primer (xi) SEQUENCE DESCRIPTION: SEQ ID NO:27:

TGATGGGGAG TCTGAATCAA                                                    20

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11CR1 primer (xi) SEQUENCE DESCRIPTION: SEQ ID NO:28:

TCTGCTTTCT TGATAAAATC CT                                                 22

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11DF1 primer (xi) SEQUENCE DESCRIPTION: SEQ ID NO:29:

AGCGTCCCCT CACAAATAAA                                                    20

(2) INFORMATION FOR SEQ ID NO:30:

```
    (i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11DR1 primer (xi) SEQUENCE DESCRIPTION: SEQ ID NO:30:

TCAAGCGCAT GAATATGCCT                                              20

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11EF primer (xi) SEQUENCE DESCRIPTION: SEQ ID NO:31:

GTATAAGCAA TATGGAACTC GA                                           22

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11ER primer (xi) SEQUENCE DESCRIPTION: SEQ ID NO:32:

TTAAGTTCACT GGTATTTGAA CA                                          23

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11FF primer (xi) SEQUENCE DESCRIPTION: SEQ ID NO:33:

GACAGCGATA CTTTCCCAGA                                              20

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear
```

(ii) MOLECULE TYPE: DNA (genomic)

(vi) ORIGINAL SOURCE:
            (B) STRAIN: 11FR primer (xi) SEQUENCE DESCRIPTION: SEQ ID NO:34:

TGGAACAACC ATGAATTAGT C                                              21

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11GF primer (xi) SEQUENCE DESCRIPTION: SEQ ID NO:35:

GGAAGTTAGC ACTCTAGGGA                                                20

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11GR primer (xi) SEQUENCE DESCRIPTION: SEQ ID NO:36:

GCAGTGATAT TAACTGTCTG TA                                             22

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11HF primer (xi) SEQUENCE DESCRIPTION: SEQ ID NO:37:

TGGGTCCTTA AGAAACAAA GT                                              22

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11HR primer (xi) SEQUENCE DESCRIPTION: SEQ ID NO:38:

```
TCAGGTGACA TTGAATCTTC C                                              21
```

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11IF primer (xi) SEQUENCE DESCRIPTION: SEQ ID NO:39:

```
CCACTTTTTC CCATCAAGTC A                                              21
```

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11IR primer (xi) SEQUENCE DESCRIPTION: SEQ ID NO:40:

```
TCAGGATGCT TACAATTACT TC                                             22
```

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11JF primer (xi) SEQUENCE DESCRIPTION: SEQ ID NO:41:

```
CAAAATTGAA TGCTATGCTT AGA                                            23
```

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11JR primer (xi) SEQUENCE DESCRIPTION: SEQ ID NO:42:

```
TCGGTAACCC TGAGCCAAAT                                                20
```

(2) INFORMATION FOR SEQ ID NO:43:

(i) SEQUENCE CHARACTERISTICS:
        (A) LENGTH: 20 base pairs (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11KF primer (xi) SEQUENCE DESCRIPTION: SEQ ID NO:43:

GCAAAAGCGT CCAGAAAGGA                                              20

(2) INFORMATION FOR SEQ ID NO:44:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11KR-1 primer (xi) SEQUENCE DESCRIPTION: SEQ ID NO:44:

TATTTGCAGT CAAGTCTTCC AA                                           22

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11LF-1 primer (xi) SEQUENCE DESCRIPTION: SEQ ID NO:45:

GTAATATTGG CAAAGGCATC T                                            21

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 11LR primer (xi) SEQUENCE DESCRIPTION: SEQ ID NO:46:

TAAAATGTGC TCCCCAAAAG CA                                           22

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:

-continued (B) STRAIN: 12F primer (xi) SEQUENCE DESCRIPTION: SEQ ID NO:47:

GTCCTGCCAA TGAGAAGAAA                                              20

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 12R primer (xi) SEQUENCE DESCRIPTION: SEQ ID NO:48:

TGTCAGCAAA CCTAAGAATG T                                            21

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 13F primer (xi) SEQUENCE DESCRIPTION: SEQ ID NO:49:

AATGGAAAGC TTCTCAAAGT A                                            21

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 13R primer (xi) SEQUENCE DESCRIPTION: SEQ ID NO:50:

ATGTTGGAGC TAGGTCCTTA C                                            21

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 14F primer (xi) SEQUENCE DESCRIPTION: SEQ ID NO:51:

CTAACCTGAA TTATCACTAT CA                                           22

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 14R primer (xi) SEQUENCE DESCRIPTION: SEQ ID NO:52:

GTGTATAAAT GCCTGTATGC A                                      21

(2) INFORMATION FOR SEQ ID NO:53:

(i) SEQUENCE CHARACTERISTICS:
        (A) LENGTH: 19 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 15F primer (xi) SEQUENCE DESCRIPTION: SEQ ID NO:53:

TGGCTGCCCA GGAAGTATG                                        19

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 15R primer (xi) SEQUENCE DESCRIPTION: SEQ ID NO:54:

AACCAGAATA TCTTTATGTA GGA                                23

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 16F primer (xi) SEQUENCE DESCRIPTION: SEQ ID NO:55:

AATTCTTAAC AGAGACCAGA AC                                  22

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
     (B) STRAIN: 16R primer (xi) SEQUENCE DESCRIPTION: SEQ ID NO:56:

AAAACTCTTT CCAGAATGTT GT                                              22

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 17F primer (xi) SEQUENCE DESCRIPTION: SEQ ID NO:57:

GTGTAGAACG TGCAGGATTG                                                 20

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 17R primer (xi) SEQUENCE DESCRIPTION: SEQ ID NO:58:

TCGCCTCATG TGGTTTTA                                                   18

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 18F primer (xi) SEQUENCE DESCRIPTION: SEQ ID NO:59:

GGCTCTTTAG CTTCTTAGGA C                                               21

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
         (B) STRAIN: 18R primer (xi) SEQUENCE DESCRIPTION: SEQ ID NO:60:

```
GAGACCATTT TCCCAGCATC                                              20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 19F primer (xi) SEQUENCE DESCRIPTION: SEQ ID NO:61:

CTGTCATTCT TCCTGTGCTC                                              20

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 19R primer (xi) SEQUENCE DESCRIPTION: SEQ ID NO:62:

CATTGTTAAG GAAAGTGGTG C                                            21

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 20F primer (xi) SEQUENCE DESCRIPTION: SEQ ID NO:63:

ATATGACGTG TCTGCTCCAC                                              20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 20R primer (xi) SEQUENCE DESCRIPTION: SEQ ID NO:64:

GGGAATCCAA ATTACACAGC                                              20

(2) INFORMATION FOR SEQ ID NO:65:

(i) SEQUENCE CHARACTERISTICS:
```

```
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 21F primer (xi) SEQUENCE DESCRIPTION: SEQ ID NO:65:

AAGCTCTTCC TTTTTGAAAG TC                                            22

(2) INFORMATION FOR SEQ ID NO:66:

(i) SEQUENCE CHARACTERISTICS:
        (A) LENGTH: 22 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 21R primer (xi) SEQUENCE DESCRIPTION: SEQ ID NO:66:

GTAGAGAAAT AGAATAGCCT CT                                            22

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22F primer (xi) SEQUENCE DESCRIPTION: SEQ ID NO:67:

TCCCATTGAG AGGTCTTGCT                                               20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: linear (ii) MOLECULE TYPE: DNA (genomic)

(vi) ORIGINAL SOURCE:
        (B) STRAIN: 22R primer (xi) SEQUENCE DESCRIPTION: SEQ ID NO:68:

GAGAAGACTT CTGAGGCTAC                                               20

(2) INFORMATION FOR SEQ ID NO:69:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: linear (ii) MOLECULE TYPE: DNA (genomic)
```

```
    (vi) ORIGINAL SOURCE:
         (B) STRAIN: 23F-1 primer (xi) SEQUENCE DESCRIPTION: SEQ ID NO:69:

TGAAGTGACA GTTCCAGTAG T                                              21

(2) INFORMATION FOR SEQ ID NO:70:

(i) SEQUENCE CHARACTERISTICS:
         (A) LENGTH: 23 base pairs
         (B) TYPE: nucleic acid
         (C) STRANDEDNESS: Not Relevant
         (D) TOPOLOGY: linear (ii) MOLECULE TYPE: DNA (genomic)

(vi) ORIGINAL SOURCE:
         (B) STRAIN: 23R-1 primer (xi) SEQUENCE DESCRIPTION: SEQ ID NO:70:

CATTTTAGCC ATTCATTCAA CAA                                            23

(2) INFORMATION FOR SEQ ID NO:71:

(i) SEQUENCE CHARACTERISTICS:
         (A) LENGTH: 22 base pairs
         (B) TYPE: nucleic acid
         (C) STRANDEDNESS: Not Relevant
         (D) TOPOLOGY: linear (ii) MOLECULE TYPE: DNA (genomic)

(vi) ORIGINAL SOURCE:
         (B) STRAIN: 24F primer (xi) SEQUENCE DESCRIPTION: SEQ ID NO:71:

ATGAATTGAC ACTAATCTCT GC                                             22

(2) INFORMATION FOR SEQ ID NO:72:

(i) SEQUENCE CHARACTERISTICS:
         (A) LENGTH: 21 base pairs
         (B) TYPE: nucleic acid
         (C) STRANDEDNESS: Not Relevant
         (D) TOPOLOGY: linear (ii) MOLECULE TYPE: DNA (genomic)

(vi) ORIGINAL SOURCE:
         (B) STRAIN: 24R primer (xi) SEQUENCE DESCRIPTION: SEQ ID NO:72:

GTAGCCAGGA CAGTAGAAGG A                                              21

(2) INFORMATION FOR SEQ ID NO:73:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: Other
         (B) LOCATION: 1...24
         (D) OTHER INFORMATION: BRCA1 Exon 2

(xi) SEQUENCE DESCRIPTION: SEQ ID NO:73:
```

```
GAAGTTGTCA TTTTATAAAC CTTT                                              24

(2) INFORMATION FOR SEQ ID NO:74:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 1...33
        (D) OTHER INFORMATION: BRCA1 Exon 2

(xi) SEQUENCE DESCRIPTION: SEQ ID NO:74:

AAAAAAAAAA AATGTCTTTT CTTCCCTAGT ATG                                    33

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Other
        (B) LOCATION: 1...20
        (D) OTHER INFORMATION: BRCA1 Exon 5

(xi) SEQUENCE DESCRIPTION: SEQ ID NO:75:

CTCTTAAGGG CAGTTGTGAG                                                   20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...20
        (D) OTHER INFORMATION: BRCA1 Exon 5

(xi) SEQUENCE DESCRIPTION: SEQ ID NO:76:

TTCCTACTGT GGTTGCTTCC                                                   20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...20
        (D) OTHER INFORMATION: BRCA1 Exon 6

(xi) SEQUENCE DESCRIPTION: SEQ ID NO:77:
```

```
TTTCTACTGT TGCTGCATCT                                                  20

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 6

(xi) SEQUENCE DESCRIPTION: SEQ ID NO:78:

CTAATGTGCA AACTTCCTGA G                                                21

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 11B (xi) SEQUENCE DESCRIPTION: SEQ ID NO:79:

TTACTCACTA AAGACAGAAT G                                                21

(2) INFORMATION FOR SEQ ID NO:80:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 11B (xi) SEQUENCE DESCRIPTION: SEQ ID NO:80:

CCAGAATATT CATCTACCTC A                                                21

(2) INFORMATION FOR SEQ ID NO:81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 11B
```

-continued (xi) SEQUENCE DESCRIPTION: SEQ ID NO:81:

TTACTCACTA AAGACAGAAT G                                              21

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 11B (xi) SEQUENCE DESCRIPTION: SEQ ID NO:82:

CCAGAATATT CATCTACCTC A                                              21

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 11L (xi) SEQUENCE DESCRIPTION: SEQ ID NO:83:

GTAATATTGG CAAAGGCATC T                                              21

(2) INFORMATION FOR SEQ ID NO:84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...22
        (D) OTHER INFORMATION: BRCA1 Exon 11L (xi) SEQUENCE DESCRIPTION: SEQ ID NO:84:

TAAAATGTGC TCCCCAAAAG CA                                             22

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 13

(xi) SEQUENCE DESCRIPTION: SEQ ID NO:85:

AATGGAAAGC TTCTCAAAGT A                                              21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...21
        (D) OTHER INFORMATION: BRCA1 Exon 13

(xi) SEQUENCE DESCRIPTION: SEQ ID NO:86:

ATGTTGGAGC TAGGTCTTTA C                                              21

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...20
        (D) OTHER INFORMATION: BRCA
 Exon 20

(xi) SEQUENCE DESCRIPTION: SEQ ID NO:87:

ATATGACGTG TCTGCTCCAC                                                20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...20
        (D) OTHER INFORMATION: BRCA1 Exon 20

(xi) SEQUENCE DESCRIPTION: SEQ ID NO:88:

GGGAATCCAA ATTACACAGC                                                20

(2) INFORMATION FOR SEQ ID NO:89:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other (B) LOCATION: 1...17
            (D) OTHER INFORMATION: BRCA1 ASO probe - 185delAG-Mutant (xi) SEQUENCE DESCRIPTION: SEQ ID NO:89:

ATCTTAGTGT CCCAAAT                                                    17

(2) INFORMATION FOR SEQ ID NO:90:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO 185delAG-Normal (xi) SEQUENCE DESCRIPTION: SEQ ID NO:90:

AATCTTAGAG TGTCCCA                                                    17

(2) INFORMATION FOR SEQ ID NO:91:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO T300G-Mutant (xi) SEQUENCE DESCRIPTION: SEQ ID NO:91:

CTTCACAGGG TCCTTTA                                                    17

(2) INFORMATION FOR SEQ ID NO:92:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO T300G-Normal (xi) SEQUENCE DESCRIPTION: SEQ ID NO:92:

CTTCACAGTG TCCTTTA                                                    17

(2) INFORMATION FOR SEQ ID NO:93:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:

(A) NAME/KEY: Other
        (B) LOCATION: 1...17
        (D) OTHER INFORMATION: BRCA1 ASO T>G-Mutant (xi) SEQUENCE DESCRIPTION: SEQ ID NO:93:

TCAAACAAGT TAATTTC                                                          17

(2) INFORMATION FOR SEQ ID NO:94:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...22
        (D) OTHER INFORMATION: BRCA1 ASO T>G-Normal (xi) SEQUENCE DESCRIPTION: SEQ ID NO:94:

TCAAACAAGT TAATTTC                                                          17

(2) INFORMATION FOR SEQ ID NO:95:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...17
        (D) OTHER INFORMATION: BRCA1 ASO 1136insA-Mutant (xi) SEQUENCE DESCRIPTION: SEQ ID NO:95:

CAGAAAAAAA AGGTAGA                                                          17

(2) INFORMATION FOR SEQ ID NO:96:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Other
        (B) LOCATION: 1...17
        (D) OTHER INFORMATION: BRCA1 ASO 1136insA-Normal (xi) SEQUENCE DESCRIPTION: SEQ ID NO:96:

CAGAAAAAAA GGTAGAT                                                          17

(2) INFORMATION FOR SEQ ID NO:97:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other

```
        (ix) FEATURE:
              (A) NAME/KEY: Other
              (B) LOCATION: 1...17
              (D) OTHER INFORMATION: BRCA
ASO 1294del40-Mutant (xi) SEQUENCE DESCRIPTION: SEQ ID NO:97:

GTGATGAACA AATGCCA                                                  17

(2) INFORMATION FOR SEQ ID NO:98:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: Other (ix) FEATURE:
              (A) NAME/KEY: Other
              (B) LOCATION: 1...17
              (D) OTHER INFORMATION: BRCA
ASO 1294delL40-Normal (xi) SEQUENCE DESCRIPTION: SEQ ID NO:98:

GATGACTCAC ATGATGC                                                  17

(2) INFORMATION FOR SEQ ID NO:99:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: Other (ix) FEATURE:
              (A) NAME/KEY: Other
              (B) LOCATION: 1...17
              (D) OTHER INFORMATION: BRCA1 ASO 4184del4-Mutant (xi) SEQUENCE DESCRIPTION: SEQ ID NO:99:

AGAAAATAAG AAGAGCA                                                  17

(2) INFORMATION FOR SEQ ID NO:100:

(i) SEQUENCE CHARACTERISTICS:
              (A) LENGTH: 17 base pairs
              (B) TYPE: nucleic acid
              (C) STRANDEDNESS: single
              (D) TOPOLOGY: linear (ii) MOLECULE TYPE: Other (ix) FEATURE:
              (A) NAME/KEY: Other
              (B) LOCATION: 1...17
              (D) OTHER INFORMATION: BRCA1 ASO 4184del4-Normal (xi) SEQUENCE DESCRIPTION: SEQ ID NO:100:

AGAAAATAAT CAAGAAG                                                  17

(2) INFORMATION FOR SEQ ID NO:101:

(i) SEQUENCE CHARACTERISTICS:
              (A) LENGTH: 17 base pairs
              (B) TYPE: nucleic acid
              (C) STRANDEDNESS: single
              (D) TOPOLOGY: linear
```

(ii) MOLECULE TYPE: Other (ix) FEATURE:
            (A) NAME/KEY: Other
            (B) LOCATION: 1...17
            (D) OTHER INFORMATION: BRCA1 ASO C4446T-Mutant (xi) SEQUENCE DESCRIPTION: SEQ ID NO:101:

AGGACCTGTG AAATCCA                                                              17

(2) INFORMATION FOR SEQ ID NO:102:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO C4446T-Normal (xi) SEQUENCE DESCRIPTION: SEQ ID NO:102:

AGGACCTGCG AAATCCA                                                              17

(2) INFORMATION FOR SEQ ID NO:103:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO 5382insC-Mutant (xi) SEQUENCE DESCRIPTION: SEQ ID NO:103:

AGAGAATCCC CAGGACA                                                              17

(2) INFORMATION FOR SEQ ID NO:104:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...17
            (D) OTHER INFORMATION: BRCA1 ASO 5382insC-Normal (xi) SEQUENCE DESCRIPTION: SEQ ID NO:104:

AGAGAATCCC AGGACAG                                                              17

(2) INFORMATION FOR SEQ ID NO:105:

(i) SEQUENCE CHARACTERISTICS:
            (A) LENGTH: 57 base pairs
            (B) TYPE: nucleic acid
            (C) STRANDEDNESS: single (D) TOPOLOGY: linear (ii) MOLECULE TYPE: Other (ix) FEATURE:
            (A) NAME/KEY: Other
            (B) LOCATION: 1...57
            (D) OTHER INFORMATION: Primer (11)F-1(forward)

(xi) SEQUENCE DESCRIPTION: SEQ ID NO:105:

GCTAATACGA CTCACTATAG GAACAGACCA CCATGGCTTG TGAATTTTCT GAGACGG           57

(2) INFORMATION FOR SEQ ID NO:106:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...21
            (D) OTHER INFORMATION: Primer (11)R-1b(reverse)

(xi) SEQUENCE DESCRIPTION: SEQ ID NO:106:

ATTCTGCAAA TACTGAGCAT C                                                  21

(2) INFORMATION FOR SEQ ID NO:107:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...59
            (D) OTHER INFORMATION: Primer (11)F-2(forward)

(xi) SEQUENCE DESCRIPTION: SEQ ID NO:107:

GCTAATACGA CTCACTATAG GAACAGACCA CCATGGACAA TTCAAAAGCA CCTAAAAAG         59

(2) INFORMATION FOR SEQ ID NO:108:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...21
            (D) OTHER INFORMATION: Primer (11)R-2B(reverse)

(xi) SEQUENCE DESCRIPTION: SEQ ID NO:108:

ATTACCTGGT TACTGCAGTC A                                                  21

(2) INFORMATION FOR SEQ ID NO:109:

(i) SEQUENCE CHARACTERISTICS:
            (A) LENGTH: 58 base pairs
            (B) TYPE: nucleic acid -continued

```
            (C) STRANDEDNESS: single
            (D) TOPOLOGY: linear (ii) MOLECULE TYPE: Other (ix) FEATURE:
            (A) NAME/KEY: Other
            (B) LOCATION: 1...58
            (D) OTHER INFORMATION: Primer (11)F-3(forward)

(xi) SEQUENCE DESCRIPTION: SEQ ID NO:109:

GCTAATACGA CTCACTATAG GAACAGACCA CCATGGCACC ACTTTTTCCC ATCAAGTC           58

(2) INFORMATION FOR SEQ ID NO:110:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Other (ix) FEATURE:
            (A) NAME/KEY: Other
            (B) LOCATION: 1...23
            (D) OTHER INFORMATION: (11)R-3(reverse)

(xi) SEQUENCE DESCRIPTION: SEQ ID NO:110:

TTATTTTCTT CCAAGCCCGT TCC                                                23
```